US006268168B1

(12) United States Patent
Farb et al.

(10) Patent No.: US 6,268,168 B1
(45) Date of Patent: Jul. 31, 2001

(54) CELLULAR PHYSIOLOGY WORKSTATIONS FOR AUTOMATED DATA ACQUISTION AND PERFUSION CONTROL

(75) Inventors: David H. Farb, Cambridge; Nader Yaghoubi, Brookline; Terrell T. Gibbs, Boston, all of MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 09/519,109

(22) Filed: Mar. 6, 2000

Related U.S. Application Data

(62) Division of application No. 08/888,691, filed as application No. PCT/US96/18832 on Nov. 8, 1996, now Pat. No. 6,048,722.
(60) Provisional application No. 60/006,326, filed on Nov. 8, 1995.

(51) Int. Cl.[7] .................. C12Q 1/02; C12Q 1/00; C12M 3/00
(52) U.S. Cl. ................ 435/29; 435/4; 435/284.1; 435/286.5; 435/283.1; 435/287.1
(58) Field of Search .................. 435/29, 4, 287.1, 435/283.1, 286.5, 284.1

(56) References Cited

U.S. PATENT DOCUMENTS

| | | | |
|---|---|---|---|
| 4,530,907 | 7/1985 | Peterson et al. | 435/287.1 |
| 4,650,766 | 3/1987 | Harm et al. | 435/287.1 |
| 4,734,372 | 3/1988 | Rotman | 435/287.1 |
| 5,262,128 | 11/1993 | Leighton et al. | 435/283.1 |
| 5,312,731 | 5/1994 | Engstrom | 435/33 |
| 5,449,492 | 9/1995 | Krishtal | 435/283.1 |
| 5,496,697 | 3/1996 | Parce et al. | 435/287.1 |
| 5,612,188 | 3/1997 | Shuler et al. | 435/286.5 |
| 5,621,007 | 4/1997 | Gribkoff et al. | 514/387 |
| 6,048,722 | * 4/2000 | Farb et al. | 435/29 |

FOREIGN PATENT DOCUMENTS

| | | |
|---|---|---|
| 1169341 | 6/1984 | (CA) . |
| 2431198 | 1/1976 | (DE) . |
| 1346672 | 10/1987 | (SU) . |

OTHER PUBLICATIONS

Madeja et al., *J. Neuroscience Methods*. 38: 267–269(Jul. 1991).

Derwent Abstract, AN 1982–05362E of Physiology Inst. SU 819169 (Apr. 7, 1981).

* cited by examiner

*Primary Examiner*—Louise N. Leary
(74) *Attorney, Agent, or Firm*—Kevin M. Farrell

(57) ABSTRACT

Cellular physiology workstations for automated data acquisition and perfusion control are described. The cellular physiology workstation may be used for physiological and electrophysiological experiments. Methods for employing such cellular physiology workstations in physiological and electrophysiological experiments are also disclosed. The cellular physiology workstations comprise one or more recording chambers each for holding one or more cells to be measured. One or more cells are place in each recording chamber. Perfusions means, such as an automatic perfusion system is connected to the recording chamber to perfuse the cells with a plurality of solutions containing different concentration of one or more agents to be tested. Biosensors, such as patch clamps, electrodes, or microscopes are positioned to detect a response from the cell. The cellular physiology workstation may optionally comprise injecting means for introducing an injection solution into the cell before and during analysis.

25 Claims, 19 Drawing Sheets

Microfiche Appendix Included
(1 Microfiche, 18 Pages)

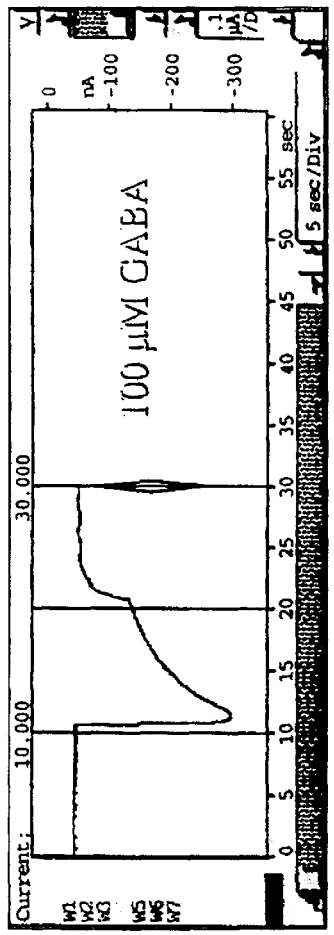
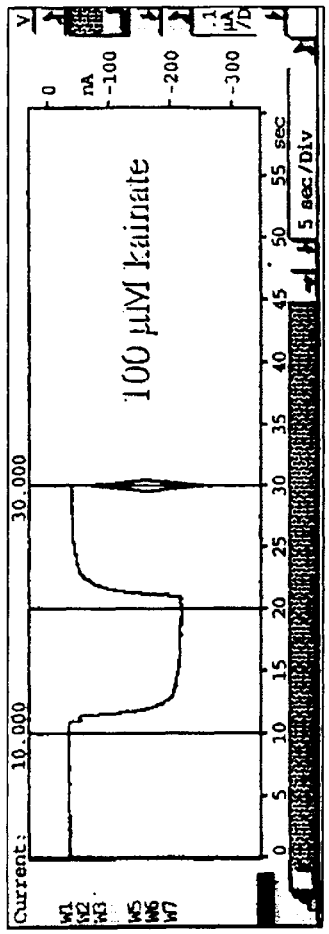
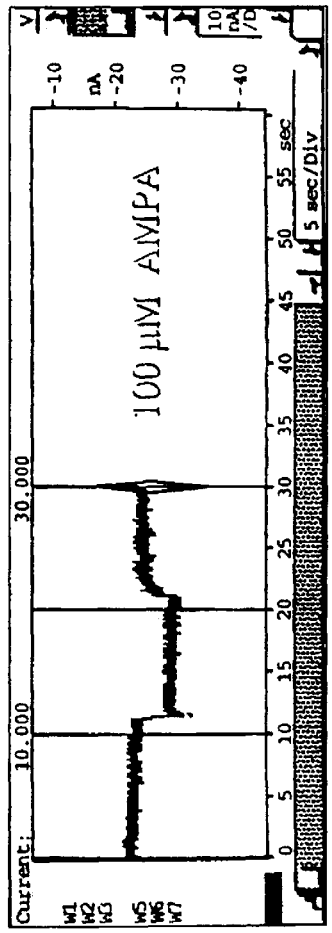
*Fig. 7A*  *Fig. 7B*  *Fig. 7C*

CELLULAR PHYSIOLOGY WORKSTATIONS FOR AUTOMATED DATA ACQUISTION AND PERFUSION CONTROL

RELATED APPLICATIONS

This application is a Divisional of U.S. application Ser. No. 08/888,691, filed Jul. 7, 1997, now U.S. Pat. No. 6,048,722, which claims priority to International Application No. PCT/US96/18832, filed Nov. 8, 1996, and to U.S. Provisional Application No. 60/006,326, filed Nov. 8, 1995.

RIGHTS IN THE INVENTION

This invention was made, in part, with United States Government support under grant number MH-49469, awarded by the National Institute of Mental Health, and the United States Government has certain rights in the invention.

MICROFICHE APPENDIX

One microfiche appendix is filed with this application. Microfiche appendix A contains a total of 1 microfiche and 18 frames.

BACKGROUND

1. Field of the Invention

The present invention relates to apparatuses for data acquisition and perfusion control in the analysis of cellular physiology and electrophysiology and to methods for automated perfusion and membrane voltage and current measurement for physiological and electrophysiological analysis.

2. Description of the Background

Cell membranes communicate information from the extracellular environment by means of receptor and channel proteins located within the cell membrane. Receptor proteins are gated by molecules which can bind to the receptor and signal that a binding event has taken place, often by triggering the opening of ion channels through which ions such as sodium and chloride ions can flow. Ionic flux across a cell membrane generates electrical current that can be measured with appropriate recording equipment. Electrophysiological analysis is widely used today to study the pharmacology and biophysics of membrane proteins.

An expression system utilizing unfertilized eggs, or oocytes, taken from the South African clawed frog, *Xenopus laevis*, is a preferred material for electrophysiological studies of receptor and ion channel function. Xenopus oocytes have the ability to synthesize functional proteins when microinjected with exogenous mRNA or cDNA constructs.

In electrophysiological analysis, an oocyte is electrically connected to intracellular voltage and current measuring and clamping devices. Detection of an electrophysiological response may comprise steps of applying appropriate receptor ligands and adjusting the holding potential manually and measuring any changes in membrane voltage or current.

Recently, electrophysiological analysis of Xenopus oocytes has been actively applied to many fields. In particular, electrophysiological analysis has been used for the study of membrane protein function, such as the function and pharmacology of membrane receptors, voltage-gated ion channels, molecular transporters and ion pumps. Defined combinations of recombinant subunits, chimeric proteins, or mutagenized constructs can be efficiently reconstituted in the oocyte membrane for electrophysiological analysis. For such analysis, the oocyte response may be monitored using intracellular recording, patch clamp and internal perfusion techniques.

It has been difficult to achieve a highly reproducible and reliable assay or to achieve quantitative analysis of electrophysiological response by conventional manual pension and membrane potential measurement techniques. These techniques have many shortcomings because of variabilities due to human errors, operator fatigue and inconsistencies between operators, and less than optimal reproducibility and reliability. Further, the perfusion and detection steps typically require long and complicated manual manipulations which create additional problems. The cultured cell becomes less viable with time and it is difficult to control the temperature and oxygen tension. The limited dexterity of even the most experienced operator limits the number of experiments may be performed on one cell. Reliance on human operators has resulted in reaction times that are considerably longer than theoretically possible.

Conventional systems for analysis of cells have attempted to address some of the problems of automated cell analysis. These systems have suffered generally from inability to individually measure a physiological response of a cell. Examples of systems that do not address individual physiological measurements include Kearney, Engström, Fränzl al. and Capco et al.

Kearney (U.S. Pat. No. 5,424,209), discloses a system for culturing and testing of cells. This culturing and testing system was designed for the culturing and testing of cell populations and not individual cells. Engström (U.S. Pat. No. 5,312,731) discloses a method and apparatus for studying a reaction pattern of a cell or cell aggregate during perfusion with different media. The system is limited to analysis of cell response of a through transmission microscopy. Fränzl et al., (U.S. Pat. No. 5,432,086) discloses an apparatus for the automatic monitoring of microorganism culture. The system is limited to the monitoring of microorganism growth and multiplication by an-impedance measuring process. Capco et aL, (U.S. Pat. No. 4,983,527) discloses a method for detection of tumor promoting compounds. Amphibian oocytes are contacted to a tumor promoting compound and the oocytes are examined visually to detect a change in the size of the light/dark hemisphere of the oocyte. Capco's disclosed method is limited to contacting the oocytes to one solution comprising a candidate tumor promoting compound.

SUMMARY OF THE INVENTION

The present invention overcomes the problems and disadvantages associated with current strategies and designs and provides novel apparatus and methods for the study of membrane physiology.

One embodiment of the invention is directed to cellular physiology workstations that enable automated execution of experimental protocols for electrophysiological experiments and for the development of more complex protocols based on extended recording sessions. As currently developed for oocyte electrophysiology, the apparatus comprises one or more custom-built recording chambers, a perfusion control system designed for rapid application of about 2 to about 16 or more solutions under automated control, software-based virtual instrumentation developed to automate the execution of experimental protocols, and a data acquisition and control platform which integrates the entire system. The system is fully customizable through a sophisticated object-oriented programming language and can be easily adapted to applications such as patch clamp electrophysiology, calcium imaging studies, confocal microscopy and other applications where perfusion control and data acquisition need to be tightly integrated.

Another embodiment of the invention is directed to apparatus for reproducibly detecting the electrical response of a cell to an agent. The apparatus comprises a plurality of recording chambers. Each chamber is designed to contain one or more cells such as, for example, one or more Xenopus oocytes. Means are provided to perfuse each recording chamber with a plurality of perfusion solutions. Each perfusion solution may contain a different concentration of one or more agent. A plurality of electrodes such as, for example, a voltage measuring electrode, a current injecting electrode or a glass patch electrode, may be connected to each cell to measure the electrical response of the cell to the presence, absence or change in concentration of the agent. The electrical response may also be measured at various holding potentials.

Another embodiment of the invention is directed to automated apparatuses for electrophysiological measurement which comprises injecting means, such as a needle, for delivering an injection solution into the cell. The injection solution may comprise a second agent, a protein, a nucleic acid or a combination thereof. The nucleic acid may be, for example, DNA, RNA or PNA. PNAs, peptide nucleic acids or protein nucleic acids, are synthetic polymers capable of hybridizing in a sequence specific manner with natural nucleic acids.

Another embodiment of the invention is directed to methods for reproducibly detecting a physiological response of a cell to a agent. A cell such as, for example, a Xenopus oocyte, is perfused using an automated perfusion system with a plurality of solutions, which may comprise different concentrations of one or more agents, and the electrophysiological response of the cell measured. The automated perfusion control system may be, for example, a gravity fed flow through perfusion system. The automated perfusion control system may have an optimized lag time of less than about 100 milliseconds and a rise time of less than about 140 milliseconds such as less than about 70 milliseconds.

Another embodiment of the invention is directed to assays for detecting a substance which affects cellular physiology. A cell is injected with a nucleic acid such as, for example, DNA or RNA encoding a membrane receptor. The cell is perfused with a plurality of solutions comprising different concentration of said substance using an automated perfusion system. A change in cellular electrophysiology of the cell is detected to determine the effect of the substance. The period of time between the injecting step and the perfusing and measuring steps may be between about one hour to about 15 days.

Another embodiment of the invention is directed to a substance detected by the assay. A candidate substance is used and the assay is performed to detect a desirable effect. A substance capable of inducing a desirable effect is identified by the assay.

Another embodiment of the invention is directed to a kit for performing the assay. The kit may comprise reagents and biosensors for the performance of the assay.

Other embodiments and advantages of the invention are set forth, in part, in the description which follows and, in part, will be obvious from this description and may be learned from practice of the invention.

DESCRIPTION OF THE DRAWINGS

FIG. 7 depicts responses for several ligand-gated ion channels expressed after injection of the oocytes with rat brain mRNA.

DETAILED DESCRIPTION OF THE PREFERRED EMBODIMENTS

Figure 1:
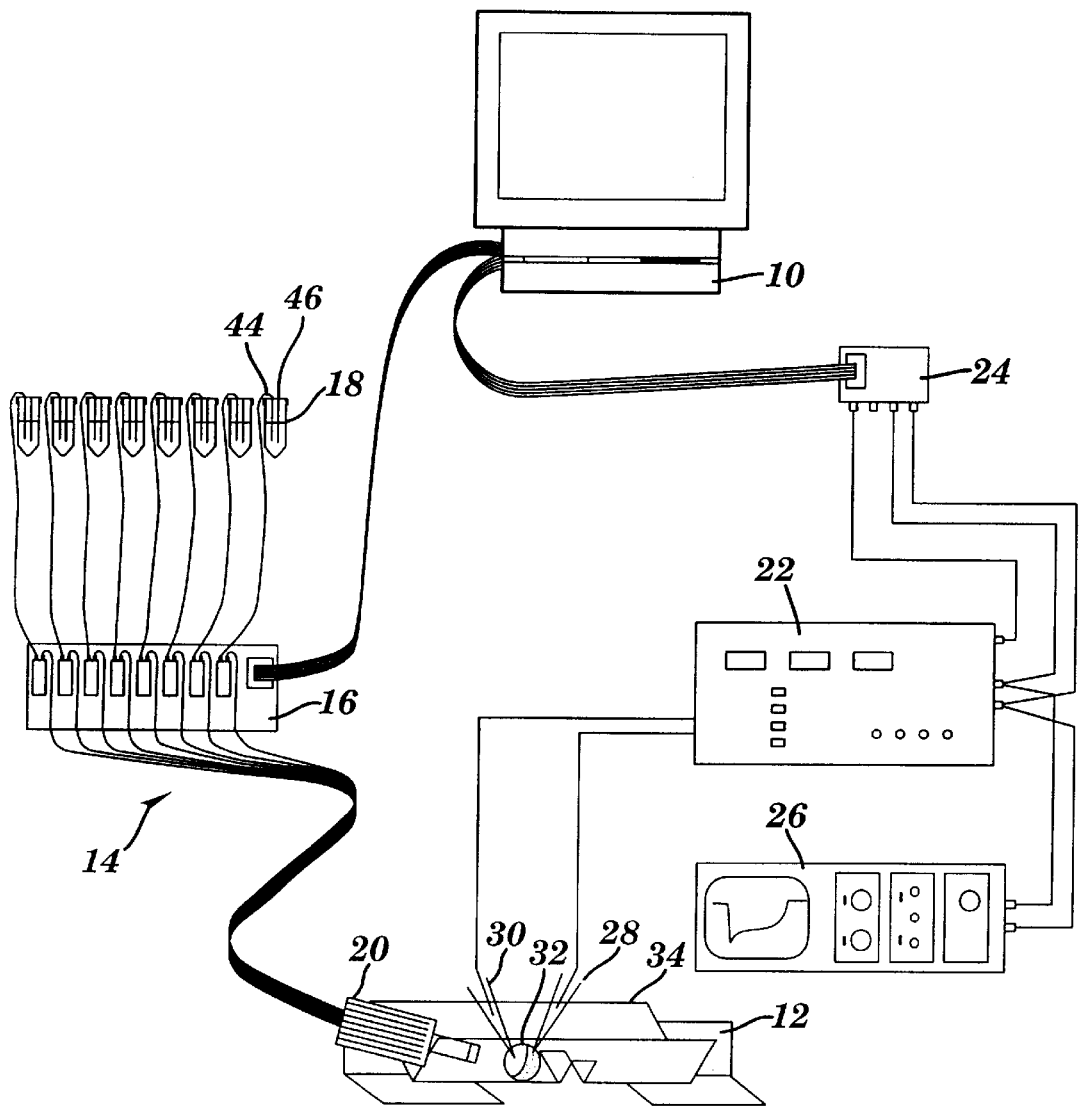
FIG. 1 depicts an automated oocyte perfusion control system according to one embodiment of the present invention.

Performing multiple electrophysiological measurement on a plurality of cells while maintaining consistency between individual experiments is problematic. Difficulties associated with reproducibility and reliability render any more than two or three measurements suspect. The present invention overcomes these problems using automated perfusion systems and methods that are capable of controlled and consistent perfusions on a plurality of recording chambers.

The cellular physiology workstation of the invention, when applied to electrophysiology, has several advantages. Automation allows experimenters to maximize the amount of data that can be obtained from a given cell during the limited viability of microelectrode-impaled cells. Automation also increases the speed and throughput of electrophysiological experiments while reducing errors associated with manual manipulations and waveform analysis. Manipulations required during a recording trial such as, toggling switches, applying drugs, measuring the response and timing the experiment are minimized or eliminated. Automation also enables the development of more complex protocols based on repetitive recordings that permit averaging of data before and after a given manipulation. Finally, automation of experimental protocols makes it feasible to utilize technician-level operators for the collection of electrophysiological data. This is advantageous for drug screening and receptor characterization. By minimizing timing, perfusion and instrument control manipulations, automation reduces experimenter fatigue during extended recording sessions. Protocols which are too complex, fast, or repetitive for manual performance may be preprogrammed and executed consistently and reliably with a single keypress. Further, the experimenter may focus on the hypothesis being tested rather than the mechanics of electrophysiological technique. Automation enables the precise timing of agent application, such as drug application, and improves the quality of experimental data by reducing inadvertent errors, -idiosyncratic variations in protocol between different investigators, and introduction of noise through manual manipulations. Automated waveform analysis reduces measurement errors as well as the post-processing time necessary for the analysis of experimental data, while enabling real-time evaluation of results. Additionally, the efficiency and speed of data generation are increased, thereby allowing mass, parallel screenings of large chemical libraries. This added throughput also allows the researcher the opportunity to test secondary hypotheses that might otherwise have been neglected due to recording time limitations or the tedious nature of the task. The physiology workstation is especially useful and advantageous in pharmaceutical, chemical and biotechnical research and development. The methods and apparatus of the invention is especially suited for repetitive or complex protocols, such as a drug dose response analysis.

Accordingly, the present invention provides an application-specific integrated workstation, particularly one for cellular electrophysiology such as oocyte electrophysiology, which results in a tremendous reduction in time expenditure in assembly. Additionally, the invention provides an automated workstation which provides greater efficiency and higher productivity. The workstation provides a tightly integrated system comprising recording chambers, perfusion system, data acquisition platform and instrumentation software that enables immediate experimentation without additional set up. At the same time, system flexibility is preserved by allowing selection of amplifiers, microscopes, micromanipulators and other such devices that are most appropriate for the experimenter's requirements.

The apparatuses and methods of the present invention may also be used for techniques such as, internal perfusion of oocytes, patch clamp electrophysiology, brain slice recording, receptor-ligand interactions on cell surfaces, calcium imaging studies, confocal microscopy, and in vivo microdialysis, for example. The system of the present invention may also be used to examine the function of ligand-gated ion channels, voltage-gated ion channels, G-protein coupled receptors, activities across the synapse, molecular transporters, cell-cell interactions and ion pumps. The system may also be useful for screening compound libraries to search for novel classes of compounds, screening members of a given class of compounds for effects on specific receptors, detailed pharmacological characterizations of compounds having receptor effects, rapid evaluation of $EC_{50}$ (potency) and $E_{max}$ (efficiency), investigation of interactions between receptors and rapid characterization of a series of receptor mutants. The invention provides repetitive application, dose-response data generation, evaluation of receptors expressed from poly $A^+$ mRNA, and evaluation of recombinant receptors such as, for example, γ-aminobutyric acid (GABA) receptors, kainate receptors, and N-Methyl-D-aspartic acid (NMDA) receptors.

Examples of agents that may be used for the apparatus and methods of the invention include drugs, receptor agonists, receptor antagonists, neurotransmitter, neurotransmitter analogues, enzyme inhibitors, ion channel modulators, G-protein coupled receptor modulators, transport inhibitors, hormones, peptides, toxins, antibodies, pharmaceutical agents, chemicals and combinations of these agents. Specific agents which may be used for the apparatus and methods of the invention include purinergics, cholinergics, serotonergics, dopaminergics, anesthetics, benzodiazepines, barbiturates, steroids, alcohols, metal cations, cannabinoids, cholecystokinins, cytokines, excitatory amino acids, GABAergics, gangliosides, histaminergics, melatonins, neuropeptides, neurotoxins, endothelins, NO compounds, opioids, sigma receptor ligands, somatostatins, tachykinins, angiotensins, bombesins, bradykinins, prostaglandins and combinations of these agents.

Another embodiment of the invention is directed to an automated workstation for data acquisition and perfusion control to facilitate electrophysiological measurement. A preferred apparatus and method are described in relation to Xenopus oocytes as follows, but it is clear to one of ordinary skill in the art that the described apparatus and methods are broadly applicable to many cell types.

Automated Perfusion Control System

Figure 5:
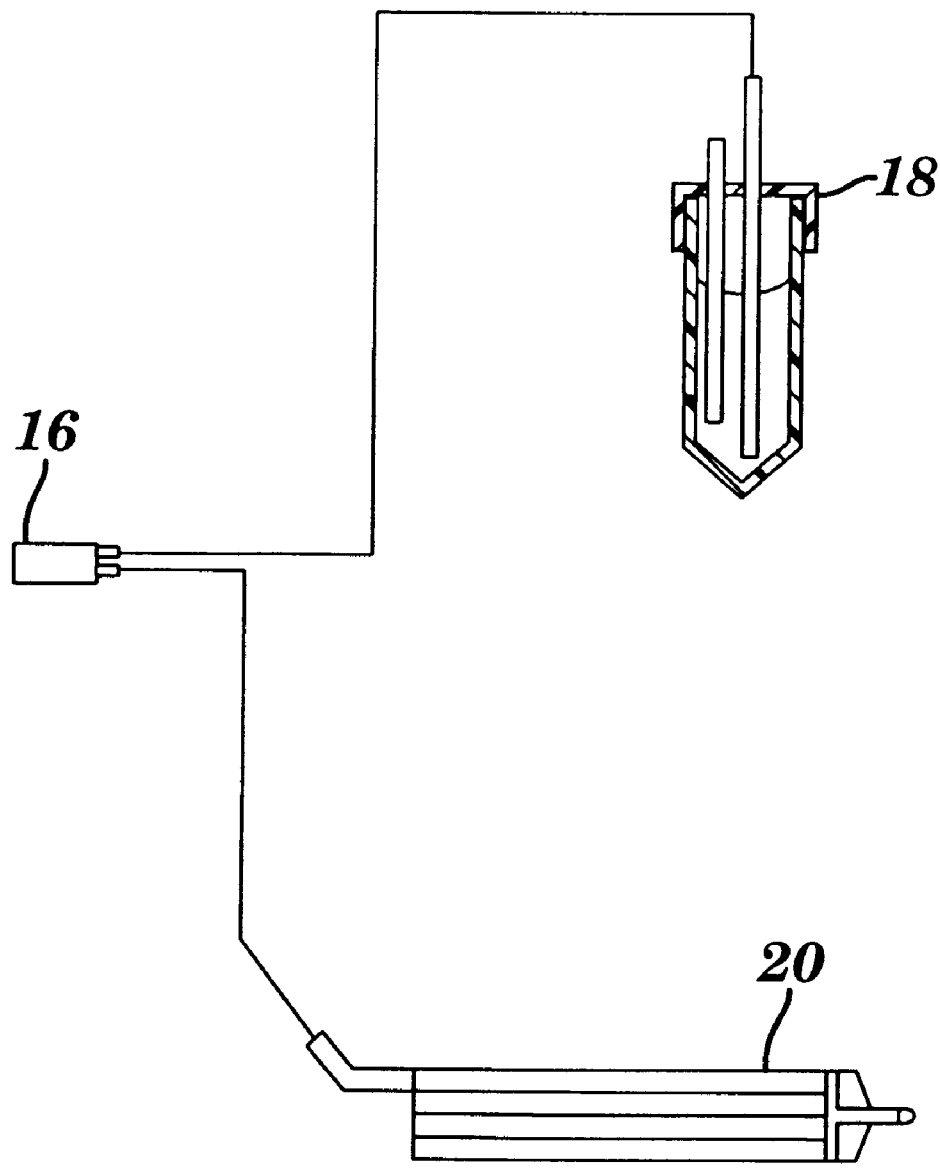
FIG. 5 depicts components of the perfusion system.

One embodiment of the present invention, depicted in FIG. 1, is an automated perfusion control system for electrophysiological studies of Xenopus oocytes. The system comprises computer 10, operating instrumentation software, recording chamber 12 designed to receive a cell such as for example, oocyte 32, and perfusion control system 14. Perfusion control system 14, depicted in FIG. 1 and FIG. 5, comprises valve controller 16, connected to and under the control of computer 10. Valve controller 16 is connected by a plurality of tubes 44 to a plurality of constant flow reservoirs 18 to multi-barrel manifold 20. Each reservoir comprises ventilation means 46 which allow gravity flow of solution from the reservoir 18, through tube 44 when valve controller 16 is open. Valve controller 16 comprises a plurality of solenoid valves. The system may also comprise voltage clamp amplifier 22 connected to and under control of computer 10 via BNC box 24. Voltage clamp amplifier 22 is connected to oscilloscope 26 and to two impaling electrodes 28 and 30 in recording chamber 12.

According to one embodiment of the present invention, the automated perfusion control system of the cellular physiology workstation may comprise a plurality of reservoirs 18 confining one or more different perfusion solutions. The reA valve 16 may be used to control delivery of the fluid to the one or more recording chambers 12. The fluid valve may be manual or machine operated. A machine operated valve may be controlled directly by computer means within the cellular physiology workstation. The automated perfusion control system may comprise between 2 to about 100 reservoirs, preferably between about 4 and about 20 reservoirs. The automated perfusion control system may optionally comprise a mixing means, such as a mixing chamber, between the fluid valve and the recording chamber.

Figure 20:
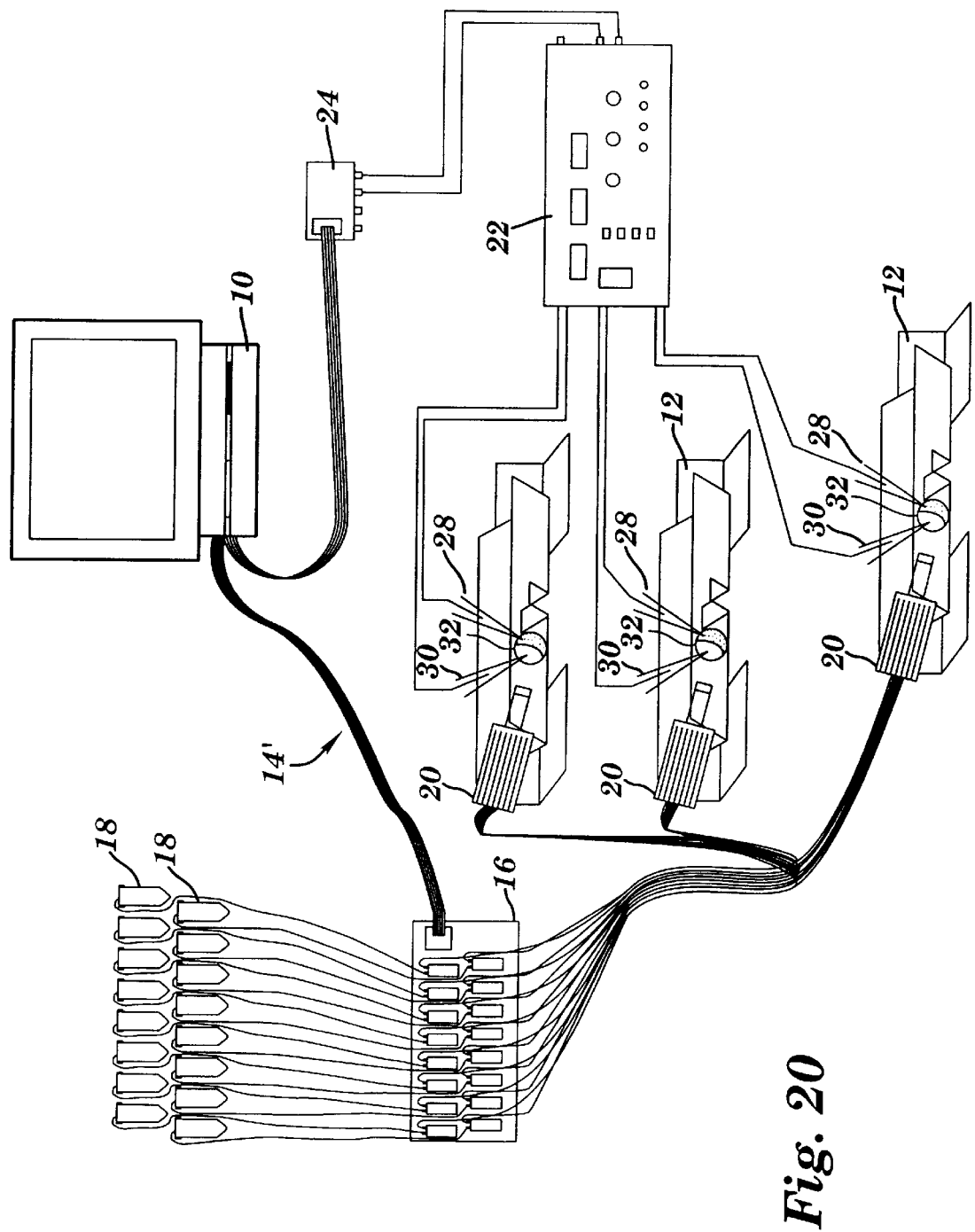
FIG. 20 depicts an alternate embodiment of the perfusion control system of the present invention.

Turning to FIG. 20, an alternate embodiment of the present invention is shown as perfusion control system 14'. This system 14' is in most respects substantially identical to perfusion control system 14, while including a plurality of recording chambers 12 and a plurality of manifolds 20.

Oocyte Preparation

In a preferred embodiment cells monitored by the cellular physiology workstation are Xenopus oocytes. Numerous methods for preparing oocytes and poly A$^+$ RNA are known to those of skill in the art One method is described as follows.

Donor animals, female oocyte positive *Xenopus laevis* frogs, are anesthetized in a solution of about 0.15% Tricaine for about 30 minutes. Ovarian sections are removed through a lateral abdominal incision, after which the incision is sutured with about 4 to about 5 stitches and the frog is allowed to recover in isolation for about 3 to about 4 hours. Ovarian lobules containing the follicular oocytes are immediately rinsed with calcium-free ND96 solution (96 mM NaCl, 1 mM $MgCl_2$, 2 mM KCl, 50 mM Hepes, 2.5 mM pyruvate) and cut into clumps of about 10 to about 20 oocytes. Following 2 mg/ml collagenase treatment (Sigma) at room temperature for about 2 hours, individual oocytes are obtained free of their follicular layer. Selected oocytes (Dumont stage V and VI) are then transferred to 60×15 mm glass petri dishes containing ND96 (96 mM NaCl, 1 mM $MgCl_2$, 2 mM KCl, 50 mM Hepes, 2.5 mM pyruvate) and maintained in an incubator at a temperature of about 18° C. to about 19° C.

Poly A$^+$ mRNA are extracted from brain tissue and neuronal cell culture using a magnetic separation protocol based on the Dynabeads Oligo (dT)25 kit (Dynal, Olso, Norway). Briefly, the protocol utilized magnetic beads that have an attached poly-T moiety which can bind poly A$^+$ mRNA for separation. Tissue is homogenized, cells are disrupted, and the lysate is added to an aliquot of Dynabeads. Magnetic separation efficiently yields mRNA that is suitable for direct injection into oocytes. Batches of about 20 to about 30 select oocytes are injected with about 50 to about 100 ng of neuronal poly A$^+$ mRNA. Alternatively, oocytes may be injected with about 30 $\mu$l to about 80 $\mu$l of RNA prepared from in vitro transcription of cDNA clones. In either case, injection may be performed using a Drummond electronic microinjector. Oocytes are then maintained at about 18° C. to about 19° C. for about 2 to about 4 days to allow protein expression prior to electrophysiological recordings. After incubation, electrophysiological analysis of expressed receptors and ion channels may be performed using a system according to the present invention.

Recording Chamber

Figure 2:
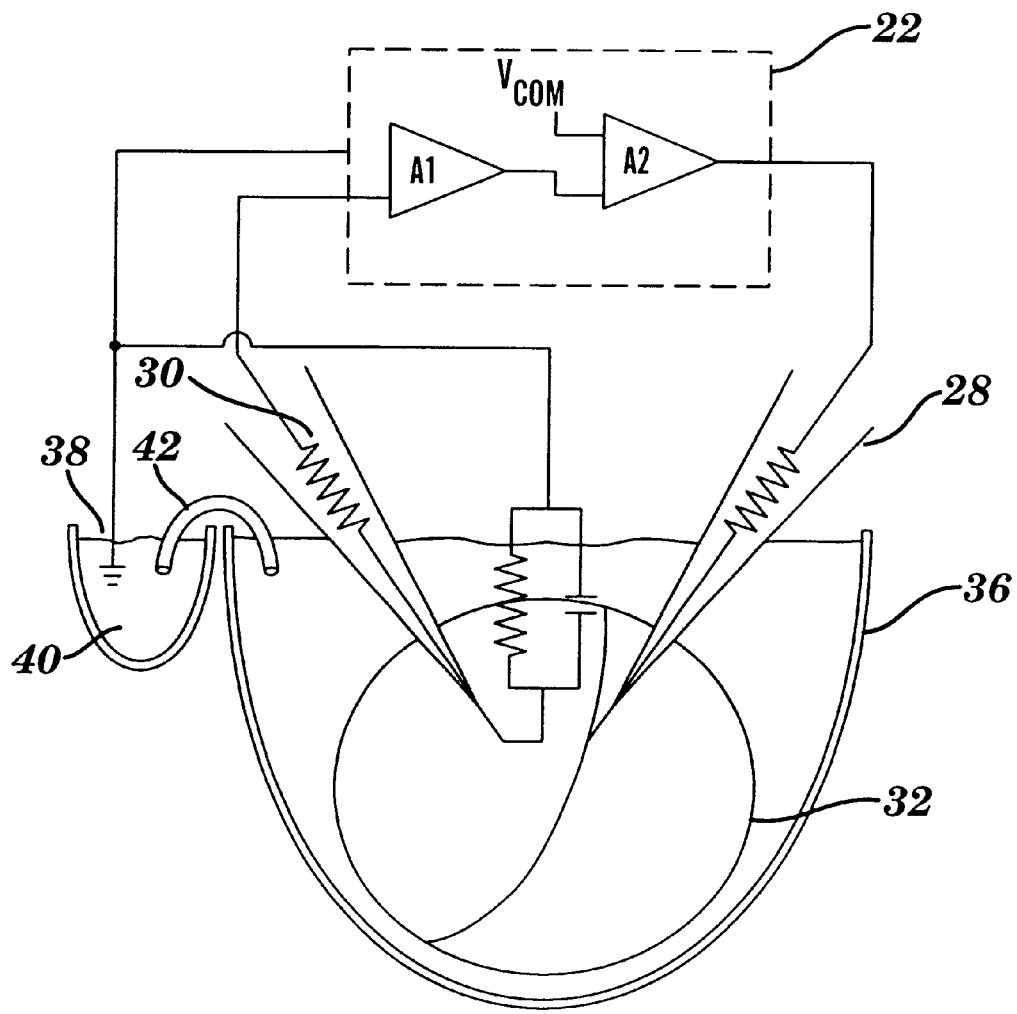
FIG. 2 depicts a voltage clamp and recording chamber connection according to one embodiment of the present invention.

A novel intracellular recording chamber for Xenopus oocyte electrophysiology has been developed to enable rapid agent application and automated control over perfusion protocols. Recording chamber 12 features a flow-through design in which gravity-feed eliminates the need for pressurization of solution containers and drop-wise removal of perfusate eliminates the need for a vacuum line. As depicted in FIG. 1 and FIG. 2, oocyte 32 sits in V-shaped groove 34 in fluid chamber 36 with a capacity of about 100 $\mu$l and is stabilized against solution flow by microelectrode impalement. The recording chamber may be adapted to accept more than one cell such as an oocyte. For example, the recording chamber may be adapted to receive about 3, about 10, about 15, or about 100 cells. Optionally, if it is desired to provide more stability against solution flow, additional devices such as needles or electrodes may be employed. This has resulted in rise times (50%–95%) of about 70 msec to about 140 msec for 100 $\mu$M GABA responses from oocytes expressing $GABA_A$ receptors, which represents the fastest rise times reported to date for Xenopus oocyte electrophysiology. The chamber is preferably made of non-conductive plastic and is clamped onto a microscope stage for stability. In one embodiment the entire chamber is plastic and electrodes 28 and 30 impale oocyte 32. The physiology workstation may comprise more than one recording chamber such as about 3, about 10, about 15, or about 100 recording chambers.

Electrodes 28 and 30 are connected to operational amplifiers A2 and A1 respectively of a voltage clamp amplifier. Operational amplifier A1 measures the voltage difference between the voltage recording electrode 30 and reference electrode 38 which is disposed in KCl well 40. KCl well 40 preferably comprises about 3M KCl and is in fluid communication with fluid chamber 36 by way of agar bridge 42. Operational amplifier A1 feeds the difference between electrode 30 and electrode 38 to operational amplifier A2. Operational amplifier A2 compares the voltage difference with the desired voltage difference, Vcom, and outputs current to injecting electrode 28 to maintain the oocyte membrane at a desired potential. In a preferred embodiment, the desired potential may be any value between about 200 mV to about −200 mV such as about −60 mV and is stepped up to any value between about 200 mV to about −200 mV such as about −100 mV during agent application to increase ionic driving forces.

The electrical response detected by the cellular physiology workstation may be a membrane potential or a membrane current. After detection the electrical response may be recorded by a recording means such as, for example, a digital recorder, a computer, volatile memory, involatile memory, a chart recorder or a combination of recording devices. The apparatus may further comprise means for controlling the temperature and oxygen level of the recording chamber.

Fluid chamber 36 has a port to which multi-barrel manifold 20 may be attached for delivery of solutions (FIG. 1). Perfusate drips through an aperture into a plastic perfusate collection chamber which feeds into a disposal bottle. Flow rates of about 1.5 ml to about 3.0 ml per minute can be achieved with adjustment of the height of the reservoir bank. Higher flow rates can be obtained with pressurization but are subjected only to the limitation of the stability and integrity of microelectrode impalement of the oocyte membrane. Minimum lag time and onset times are important for high sensitivity experiments. One advantage of the cellular physiology workstation is a recording chamber which minimizes dead volume and lag time. While pressurization and vacuum may be used, it is not required. The physiological workstation is capable of optimized lag times (valve switching to response onset time) of less than about 100 msec, such as less than 50 msec, and onset times (time to go from about 5% to about 95% of maximum amplitude) of between about 70 milliseconds to about 140 milliseconds are obtained with about 100 $\mu$M γ-aminobutyric acid (GABA) responses in oocytes injected with chick brain poly(A)$^+$ RNA. The solution exchange time is about one second for 50% exchange and about 8 seconds for 90% exchange as measured by depolarization induced by switching from normal Ringer to high potassium Ringer. An agar bridge may be used to establish electrical contact with the reference electrode through an attached KCl well.

In one embodiment, a two-electrode voltage clamp is used with two intracellular microelectrodes pulled on a Flaming-Brown micropipette puller (Model P80/PC; Sutter Instrument Co.). These electrodes have input resistances of about 2 mega-ohms to about 4 mega-ohms when filled with a solution comprising about 3M KCl. Microelectrode positioning and impalement of the oocyte may be performed under micromanipulator control.

The recording chamber may further comprise means for controling gas levels such as oxygen, nitrogen, and carbon dioxide levels. In addition the recording chamber may further comprise means for temperature control.

Configuration of the recording apparatus

The recording chamber herein described is designed to be clamped directly onto the microscope stage. The small size and novel design of this chamber permits two such chambers to be clamped side-by-side onto the stage of an unmodified Nikon SMZ-10 microscope for visual monitoring of the cells during experimentation. With slight modification and extension of the microscope stage, up to 5 such recording chambers could be so utilized. The microscope head is mounted on a sliding bracket to facilitate panning of the viewing field across the row of parallel recording chambers. For simultaneous recordings from multiple oocytes, each of these recording chambers could have two independent micromanipulators for positioning of the voltage-recording and current-injecting electrodes. At least about six micromanipulators can be positioned around the microscope stage. Ten or more micromanipulators might be positioned about the recording chamber by the careful positioning and by the use of small footprint micromanipulators.

The recording chamber may optionally comprise means for receiving and automatically positioning a cell within said recording chamber. Positioning means may comprise indentations in said recording chamber for the cells such as oocytes to settle. Other positioning means may also comprise robotic means, and artificial intelligence means for the proper positioning of the cells. Cells may be held in place after positioning by impaling probes which may or may not be a biosensor. The simplest impaling probe for immobilizing a cell may be a glass needle. Other forms of immobilizing cells such as oocyte may comprise, for example, adhesives, vacuum and indentations.

The recording chamber may optionally comprise means for positioning said one or more biosensors to detect a response from the cell. Means for positioning may be in the form of a template with biosensors spaced regularly to proximate cells positioned by the automatic cell positioning means. The biosensors may be, for example, electrodes, patch clamps or microscopes. The positioning of biosensors such as, for example electrodes, may involve the puncture and penetration of the cellular membrane. If the cells are of uniform size, such as Xenopus oocytes, the depth of penetration may be preset and fixed. Alternatively, the positioning and the depth of penetration may be determined by an automatic positioning system tailored for the specific cell type. The automatic positioning system may comprise for example, feedback and robotic mechanism which may be computer controlled for determining the proper position and depth of the probes.

Injecting Means

The physiological workstation may comprise optional means of injecting one or more injection solutions into said oocyte between the culturing and measuring step. The injection solution may comprise an agent. The agent may be a chemical, a protein or a nucleic acid.

Examples of agents that may be injection include proteins, DNA, RNA, PNA, receptor agonists, receptor antagonists, neurotransmitter, neurotransmitter analogues, enzyme inhibitors, ion channel modulators, G-protein coupled receptor modulators, transport inhibitors, hormones, peptides, toxins, antibodies, pharmaceutical agents, chemicals and combinations of these agents. Specific agents which are of interest include purinergics, cholinergics, serotonergics, dopaminergics, anesthetics, benzodiazepines, barbiturates, steroids, alcohols, metal cations, cannabinoids, cholecystokinins, cytokines, excitatory amino acids, GABAergics, gangliosides, histaminergics, melatonins, neuropeptides, neurotoxins, endothelins, NO compounds, opioids, sigma receptor ligands, somatostatins, tachykinins, angiotensins, bombesins, bradykinins, prostaglandins and combinations of these agents.

Perfusion Control System

Agent solutions are held in a plurality of plastic reservoirs, 18, each of which has a capacity of about 15 ml to about 50 ml. Reservoirs are constructed so as to maintain a constant flow rate regardless of the level of solution in each reservoir. A constant flow rate is important to ensure reproducibility of responses since onset of response is influenced by agent application rate. As depicted in FIG. 1, each reservoir 18 contains glass siphon 44 extending down through its cap into the solution and vent line 46 also extending into the solution that equilibrates chamber pressure for maintenance of constant flow rate. Solution-flow is by gravity feed and the flow rate can be controlled by adjusting the height of the reservoirs. Other method of solution flow such as vacuum, pressure or pumping may also be used. Dropwise removal of solution through the efflux line creates negative pressure in the chamber which is equilibrated by means of the vent line. In one embodiment, up to 16 different agent solutions can be prepared and placed in a rack designed to hold 16 reservoirs. Additional reservoirs may also be provided depending on the number of ports in manifold 20.

Multi-barrel manifold 20 receives input lines from the reservoirs 18 and provide a point of convergence for the different solutions. Flexible tubing, such as Tygon™, of about 0.9 mm inner diameter, carries solution from each solenoid valve of valve controller 16 to a separate barrel on manifold 20, where the lines converge to an output port that can be connected directly to recording chamber 12. Other models having additional barrels may also be used. These manifolds are custom-made from glass capillary tubing fitted with plastic tubing adaptors and have been made in 8- and 16-barrel models. These designs minimize internal dead volume so as to enable rapid agent application and minimal dilution of solutions.

Figure 4:
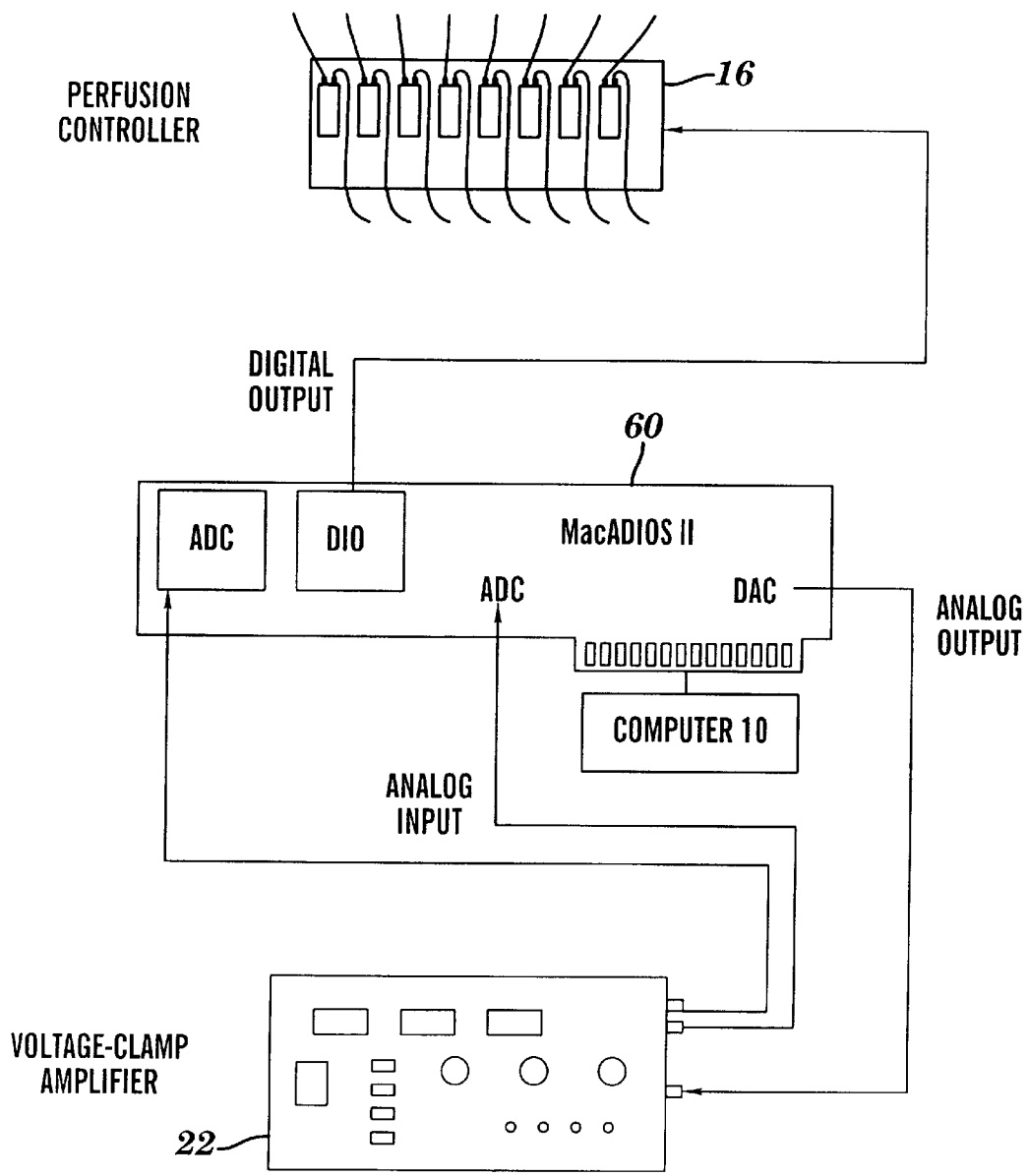
FIG. 4 depicts a block diagram showing information transfer between the system components.

The perfusion controller system functions to translate digital output from an analog/digital input/output (MacADIOS II) card 60 (FIG. 4), which is connected to computer 10, into signals which can be utilized to switch relays and solenoid valves that control perfusion. Solution flow between the constant-flow reservoirs and multi-barrel manifold is preferably controlled via 16 miniature teflon-coated solenoid valves (Lee Valve Co.; Essex, Conn.). These valves are particularly suitable because of their corrosion resistance, biocompatibility and power requirements. Other valves exhibiting these characteristics may also be used. These valves may be actuated by a direct current voltage supplied from a direct current power source which would eliminate electrical hum. Direct current power sources may be, for example, a direct current power supply or a battery. The value of the direct current voltage may be, for example, 12 volts. The valves are interfaced to the instrumentation software through an analog/digital input/output module 16 serving as valve controller 16. The digital I/O module preferably comprises a 16-channel backplane (OPT022, #PB 1 6HC) fitted with DC output modules (OPT022, #ODC5) to which the solenoid valves are connected. The digital I/O module connects to the digital out port of the analog/digital input/output (MacADIOS II) card via a flat ribbon cable and has an external 7.5V power supply (FIG. 4). The perfusion control system containing the solenoid valve assembly and the digital I/O module, is housed in a box into which flow lines enter from the agent reservoirs and exit to the multi-barrel manifold. This gravity fed perfusion control system incorporates solenoid valves to allow computer controlled switching.

In another embodiment, the perfusion control system selects between five different agent valves using transistor-based circuits in digital I/O module 16 to switch between buffers and agent inputs in response to transistor-transistor logic (TTL) signals sent on two digital lines from a data acquisition card such as a MacADIOS II card. Perfusion automation at this point provides the ability to turn on a buffer valve at the start of data acquisition, switch to a preselected agent valve at an indicated time, then switch back to buffer for agent washout, all under control of computer 10. This perfusion control system enables timely agent application protocols and removes the necessity of having to manually switch valves at appropriate times, tedious manipulations prone to experimental error and generation of noise.

Figure 3:
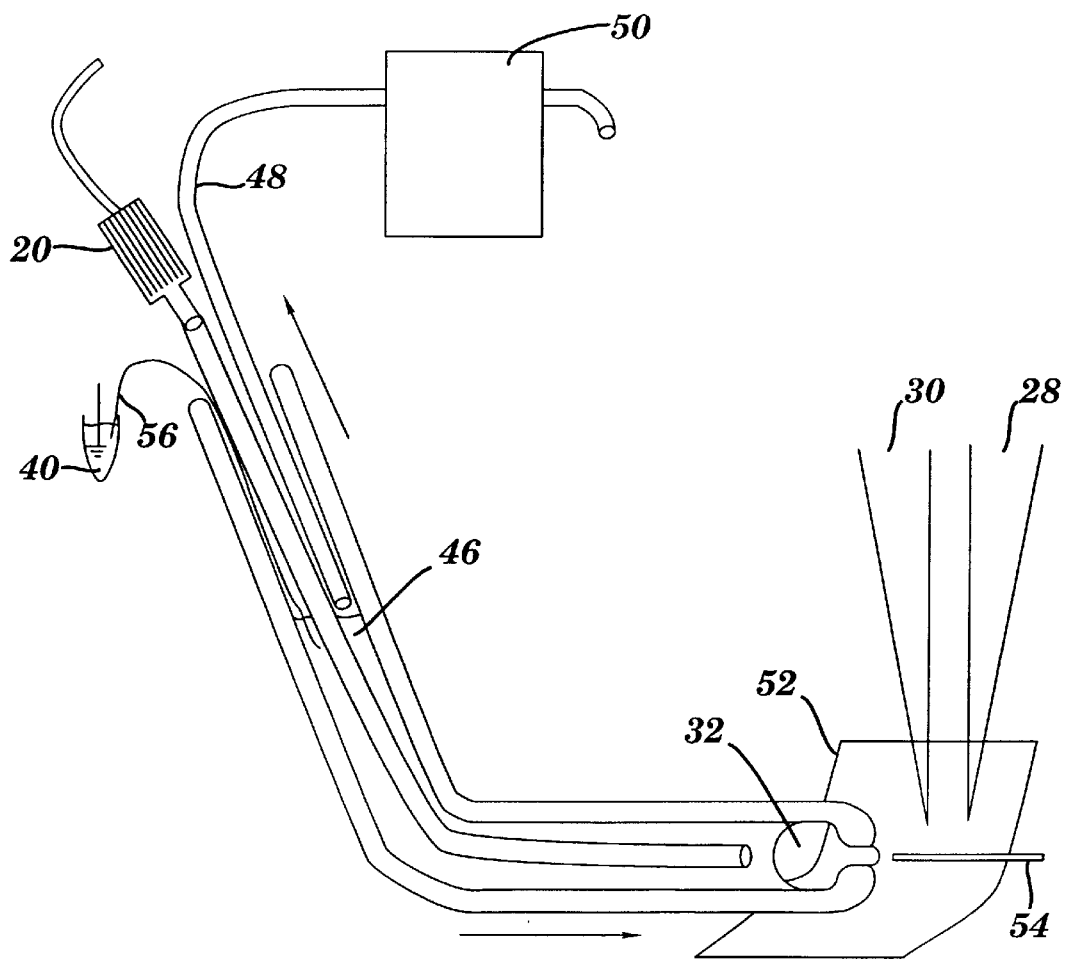
FIG. 3 depicts an internal perfusion control system according to one embodiment of the present invention.

According to another embodiment of the invention a chamber for internal perfusion of oocytes is depicted in FIG. 3. A glass perfusion chamber may be drawn from a Pasteur pipette tip that has been melted down to form a narrow aperture. Increase of fluid level in the chamber leads to formation of a high resistance seal between the devitellinized oocyte membrane and glass. Multi-port manifold 20 feeds into a perfusion line 46 which is threaded close to the oocyte 32 for agent delivery and thus external perfusion. Perfusate is removed through line 48 which maintains a constant fluid level by means of a peristaltic pump 50. Electrodes 28 and 30 may be in electrical contact with oocyte 32 by a fluid retention sleeve 52 through which a perfusion cannula 54 may be advanced for oocyte membrane rupture and internal perfusion. Chloridized silver wire 56 provides conduction between reference electrode 38 in well 40 and the chamber fluid. The internal perfusion controller of FIG. 3 allows introduction of drugs or enzymes into the oocyte cytoplasm and control of intracellular composition. The use of this perfusion controller allows control over external and internal perfusion.

Computer Control and Data Analysis Means

Figure 6:
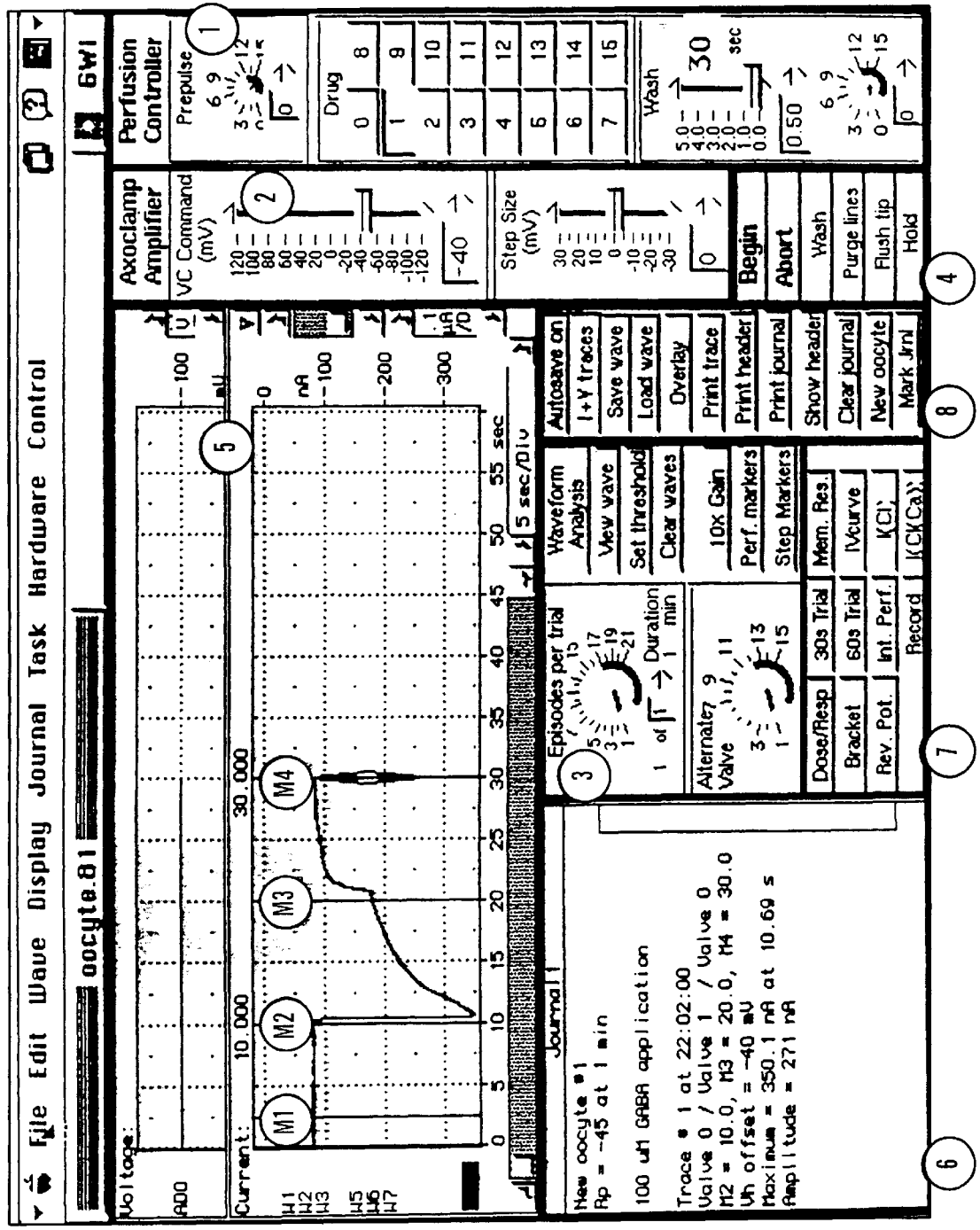
FIG. 6 depicts an instrumentation graphical user interface according to one embodiment of the present invention.

Instrumentation software, currently based on the SuperScope II v1.43 programming environment (GW Instruments; Somerville, Mass.), preferably operates on computer 10. SuperScope II provides a sophisticated graphical environment which facilitates the development of virtual instruments that are used for data acquisition and instrument control. On-screen representations of buttons, dials and sliders can be programmed to activate desired software routines using an object-oriented programming language and are used to build application-specific instruments. Other programming environments, for example, LabView™ by National Instruments (Austin, Tex.) or similar products or a general purpose programming language such as C++ can also be used to achieve to achieve similar interface. An instrument for oocyte electrophysiology may integrate agent delivery, instrument control, data acquisition and waveform analysis through an on-screen, mouse-driven interface. FIG. 6 shows a screen shot from one embodiment of such an instrument. While the virtual instrument programs such as SuperScope II or LabView provides significant convenience for the user, instrumentation software may also be written by those of skill in the art.

A virtual instrument of oocyte electrophysiology is depicted in FIG. 6. The virtual instrument was created using the SuperScope II development environment (GW Instruments, Inc.) to allow complete experimental control through a graphical user-interface. On-screen markers (M1–M4) can be moved via the mouse to set the duration of the PREPULSE PHASE (the interval between markers M1 and M2), the DRUG APPLICATION PHASE (the interval between markers M2 and M3), and the. WASHOUT PHASE (the interval between markers M3 and M4). For each phase, the perfusion controls 1 are set to select the valves controlling the wash solutions. The VC COMMAND and STEP SIZE controls 2 are used to control the voltage-clamp amplifier. The EPISODES PER TRIAL selector 3 is used to define the number of episodes to be acquired, after which the trial is initiated using the BEGIN button 4. Waveforms are displayed in real-time in the VOLTAGE and CURRENT windows 5 as they are acquired. Journal 6 automatically logs transcript of experimental session and provides waveform analysis. The protocol selection area 7 is used to select predefined protocols, while the file/log management section 8 provides file handling and data output.

The automation routines that may be implemented allow the entire recording session to be controlled through the on-screen interface by changing control knobs using the mouse. Automated protocols have been developed that can initiate and carry out dose-response, reversal potential, modulator effect and repetitive application experiments with a single keypress. Waveform analysis routines automatically measure parameters such as response amplitude, onset time and desensitization time constant and log this information directly to disk. Appendix A contains a code listing of the software implementation which may be operated on computer 10.

Computer 10 may be any computer, computer workstation, dedicated processor, microprocessor or dedicated micro-controller. In an embodiment computer 10 is a Macintosh IICi computer (Apple Computer, Cupertino, Calif.), a 68030 based computer having a minimal configuration of 8 MB RAM and an 80 MB hard drive. Voltage and current traces are acquired through analog to digital conversion means and similarly valves and perfusion controllers may be controlled through digital to analog conversion means. The analog/digital conversion means may be, for example, an analog/digital input output expansion card which may be installed into computer 10.

One preferred analog/digital input/output conversion means is a MacADIOS II data acquisition card (GW Instruments; Somerville, Mass.). This NuBus based card has an additional 12 bit A/D converter daughterboard, 2 analog output channels 8-bit digital I/O port, can be configured with additional daughterboards for enhanced functionality to facilitate independent acquisition of 2-channel data and a 16 bit digital I/O daughterboard that is used to trigger digital TTL lines for control of solenoid valves. The MacADIOS II card is interfaced to laboratory equipment through a MacADIOS APO analog I/O panel which provides electrical connections, such as BNC connections, directly to the card. As additional channels are needed, one or more secondary analog/digital converters or additional analog/digital input/output conversion cards may be added. In one embodiment, a second 12-bit A/D converter was installed to facilitate independent acquisition of 2-channel data at high speeds, while a 16-bit digital I/O daughterboard allowed individual addressing of a total of 24 digital output lines for the control of solenoid valves and other devices. Other data acquisition cards may also be used. While other computers and instrumentation software may be used, the graphical interface of the Macintosh and the SuperScope II file format simplify manipulation and plotting of waveforms. A 68030 based computer can digitize a 2-channel electrophysiological data at about 100 Hz and recorded directly to 90 MB removable data storage devices (Bernoulli cartridges; Iomega, Inc.) to facilitate convenient storage and retrieval. The implementation of the cellular physiology workstation is not computer specific, as computer technology and storage technology improve, the cellular physiology workstation may be implemented on the improved computer and storage platforms. Functions and protocols on the physiological workstation can be developed as the need arises. Computer programs and data analysis routines not available in the SuperScope II environment can be written in the C programming language for import into the existing virtual instrument.

Sample data representative of traces produced by a system according to the invention is shown in FIG. 7–FIG. 14. In FIG. 7, responses are shown for several ligand-gated ion channels that were expressed after injection of the oocytes with rat brain mRNA. Traces show responses to about 100 $\mu$M $\gamma$-aminobutyric acid (GABA) (A), about 100 $\mu$M kainate (B), and about 100 $\mu$M AMPA (C). Standard buffer solutions were used with a holding potential of about $-100$ mV. Automation enables extended recording sessions with minimal operator intervention.

Figure 8:
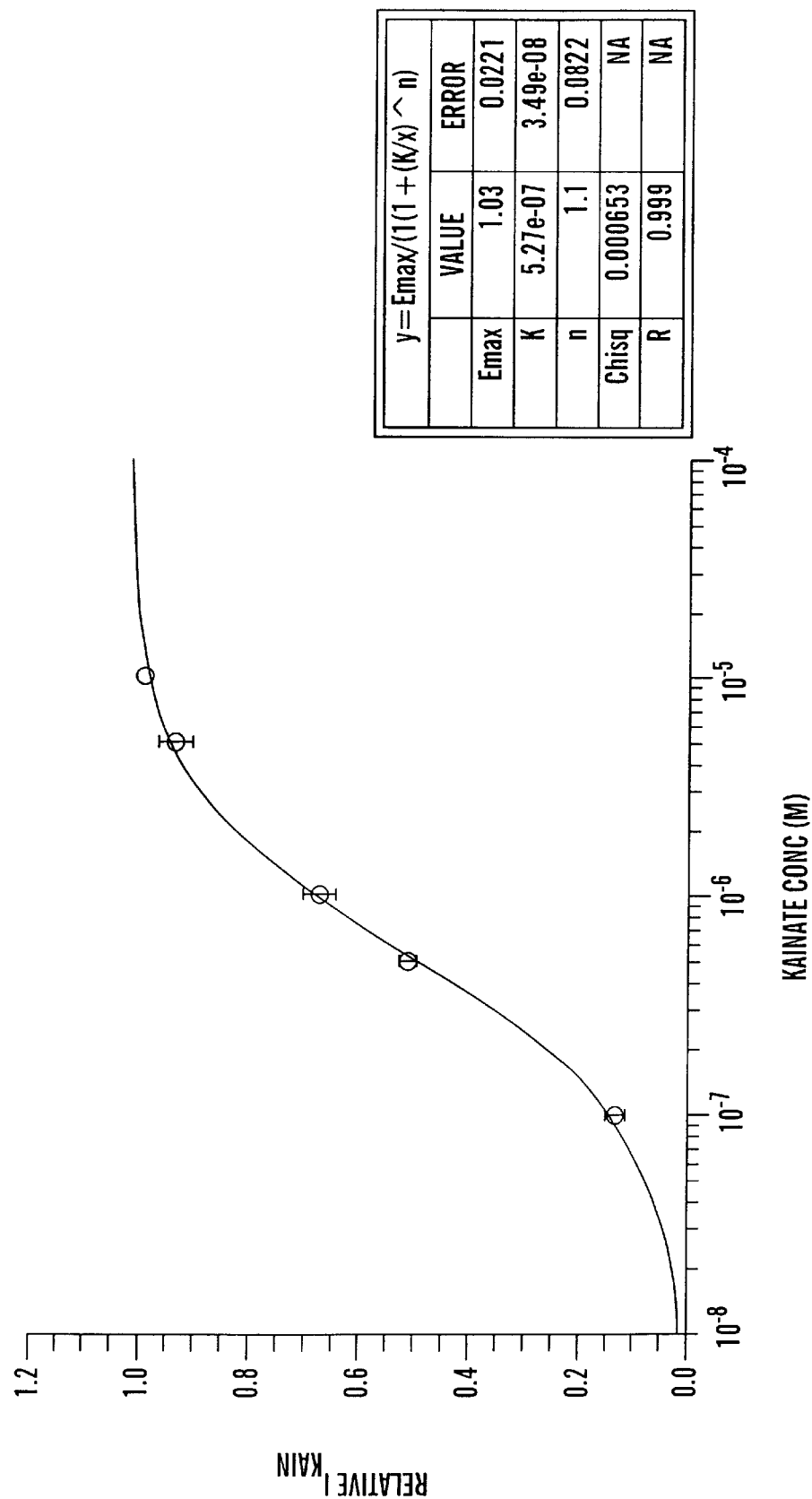
FIG. 8 depicts averaged kainate dose-response data from four oocytes injected with GluR6 cDNA.

FIG. 8 depicts the results of a test to determine the accuracy of a cellular physiology workstation according to the present invention. In FIG. 8, Averaged kainate dose-response data from 4 oocytes injected with GluR6 cRNA which yields an $EC_{50}$ of about 0.5 $\mu$M under Vh of about $-100$ mV, favorably compares to an $EC_{50}$ of about 1 $\mu$M as previously reported.

Figure 9:
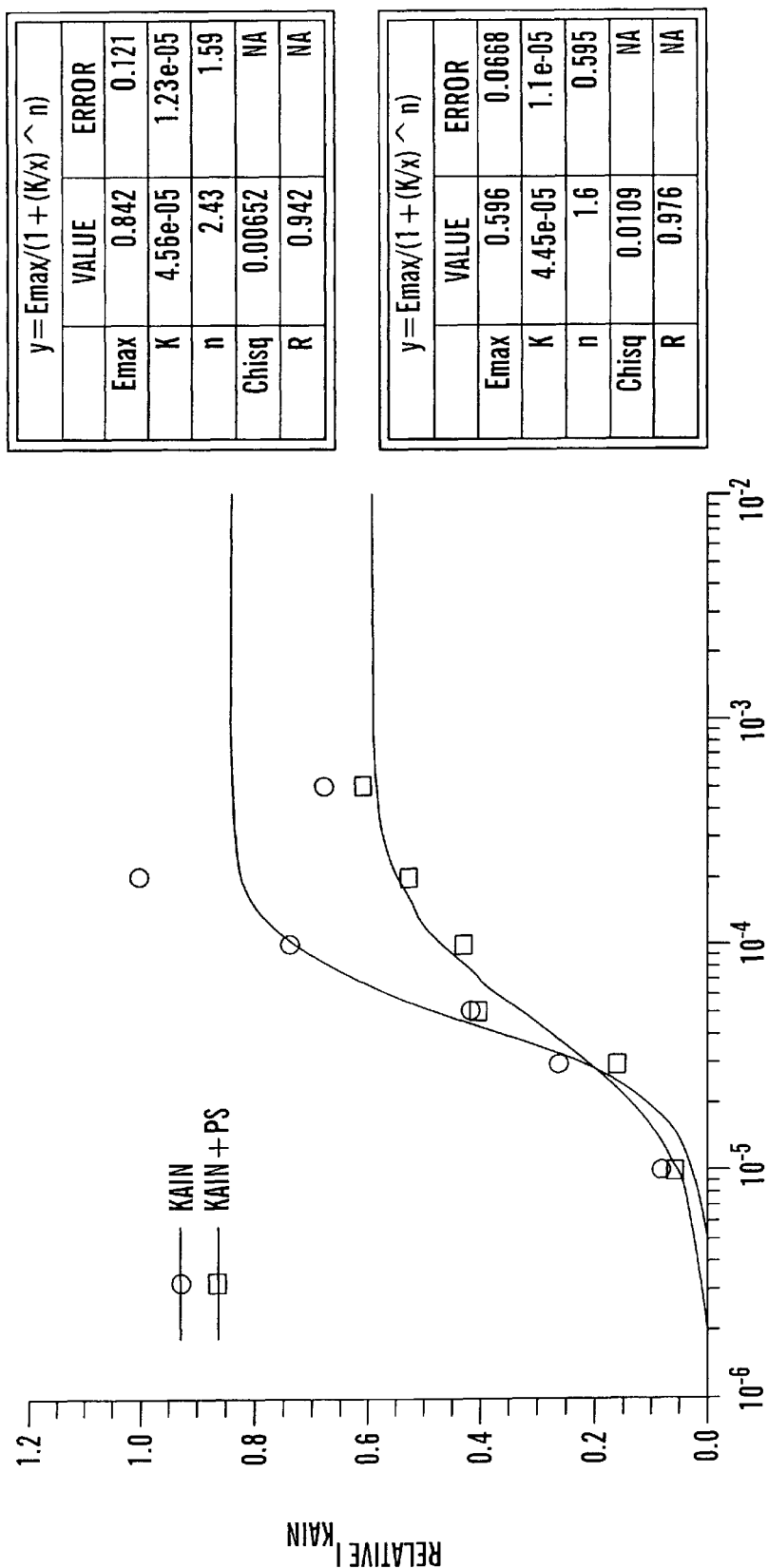
FIG. 9 depicts the effect of pregnenolone sulfate on kainate dose-response curve in oocytes injected with rat brain poly $A^+$ mRNA.

FIG. 9 depicts the effect of pregnenolone sulfate on kainate dose-response curve in oocytes injected with rat brain poly $A^+$ mRNA. Kainate dose-response curves were generated with and without the neuroactive steroid, pregnenolone sulfate (PS), and under Vh of about $-100$ mV to determine the mechanism of action. A decrease in Emax suggests a noncompetitive mechanism. This experiment demonstrates the utility of a system according to the invention for performing dose-response experiments with and without modulators.

Figure 10:
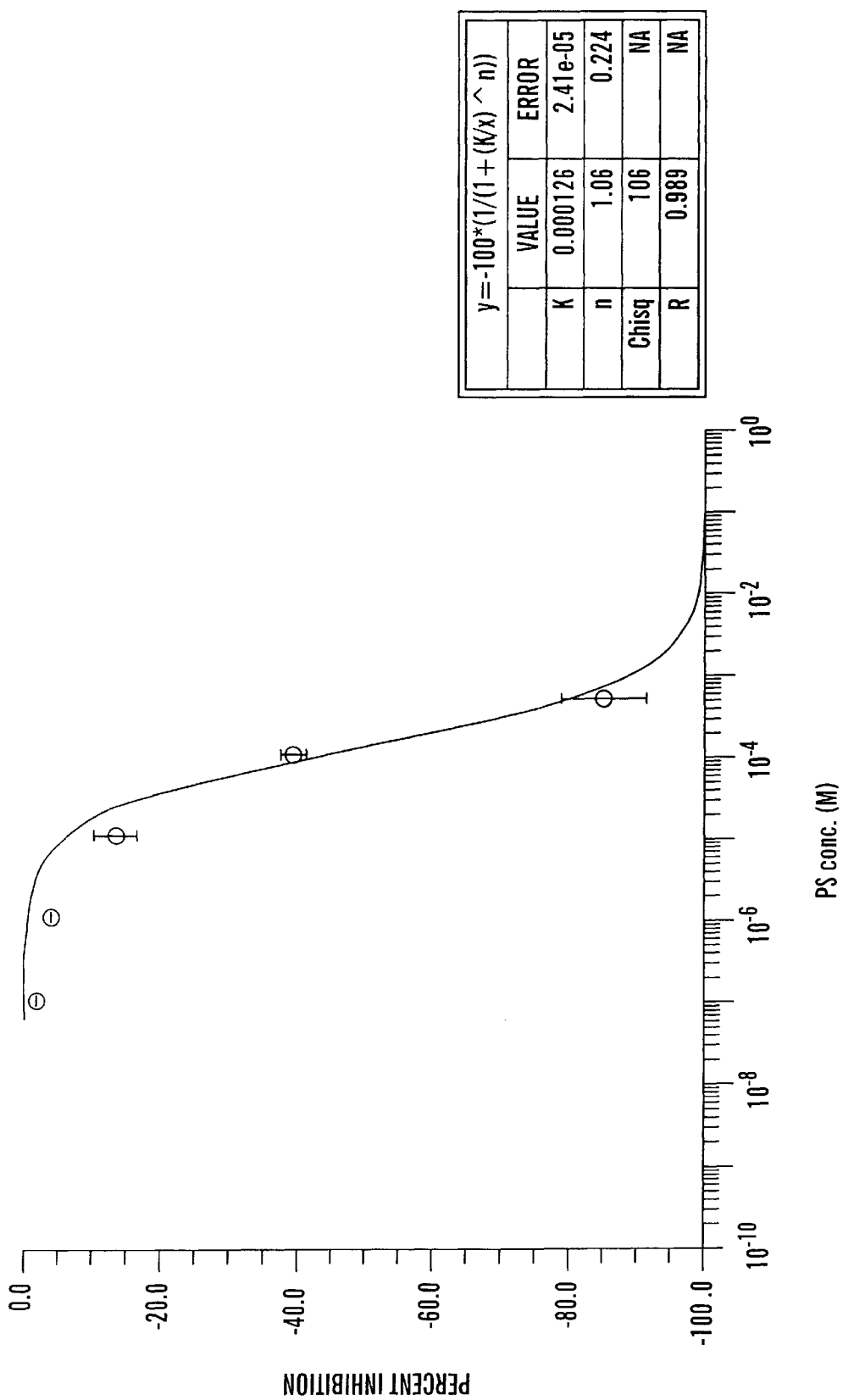
FIG. 10 depicts the measurement of pregnenolone sulfate IC50 in oocytes injected with rat brain poly $A^+$ mRNA.

FIG. 10 depicts the measurement of pregnenolone sulfate IC50 in oocytes injected with rat brain poly A* mRNA under Vh of about $-100$ mV. Pregnenolone sulfate was applied in increasing concentrations with 100 $\mu$M kainate to characterize its inhibitory effect.

Figure 11:
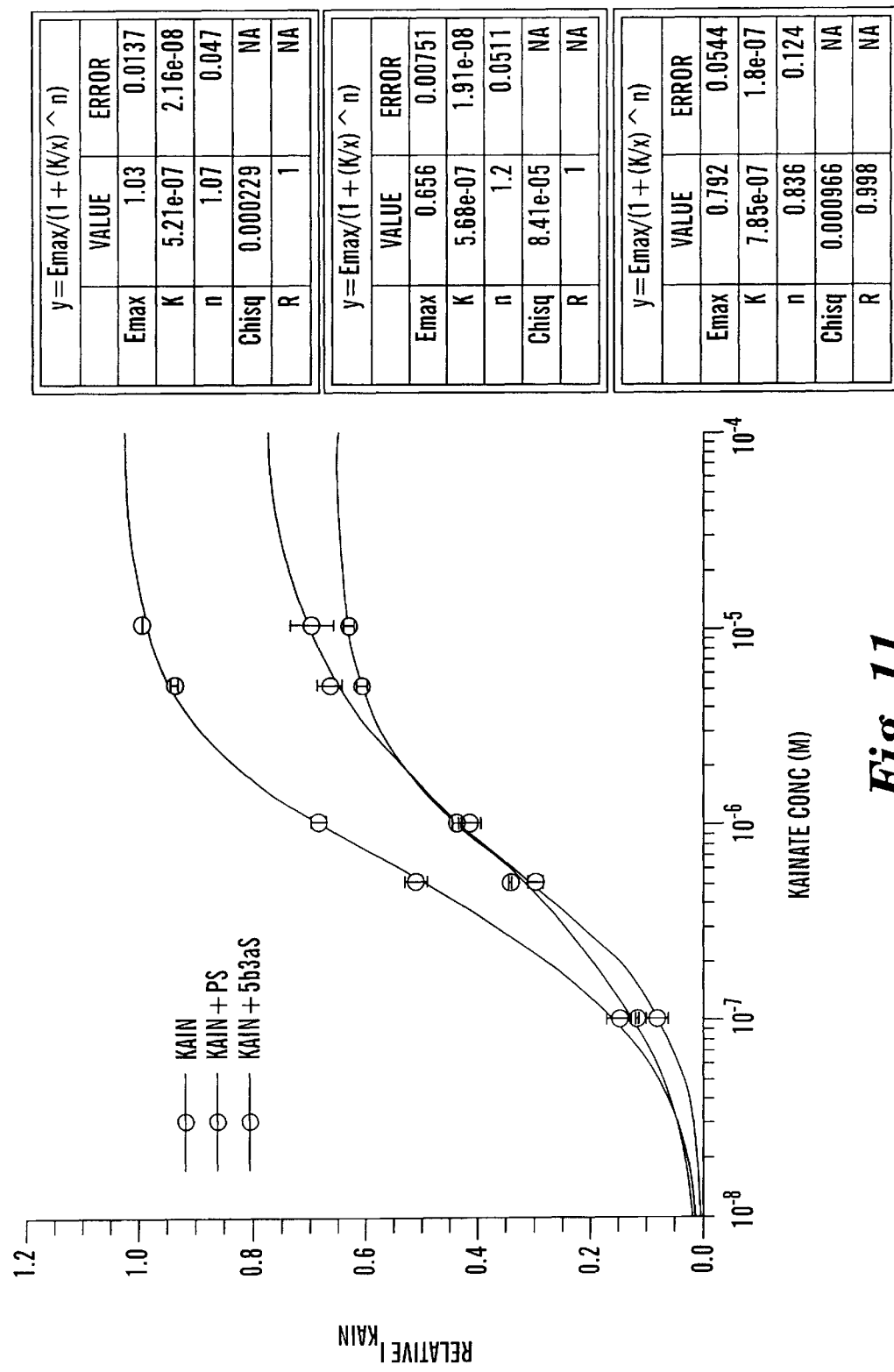
FIG. 11 depicts the effects of steroids on recombinant GluR6 kainate receptors.

FIG. 11 depicts the effects of pregnenolone sulfate and 5$\beta$3$\alpha$S on recombinant GluR6 kainate receptors. All measurements were performed under Vh of about $-100$ mV. Recombinant receptors may be rapidly characterized by utilization of automated methodologies according to the invention. The inhibitory effect of neuroactive steroids PS and 5$\beta$3$\alpha$S are shown in this experiment. These steroids decrease the maximal response to kainate with no change in kainate EC50.

Figure 12:
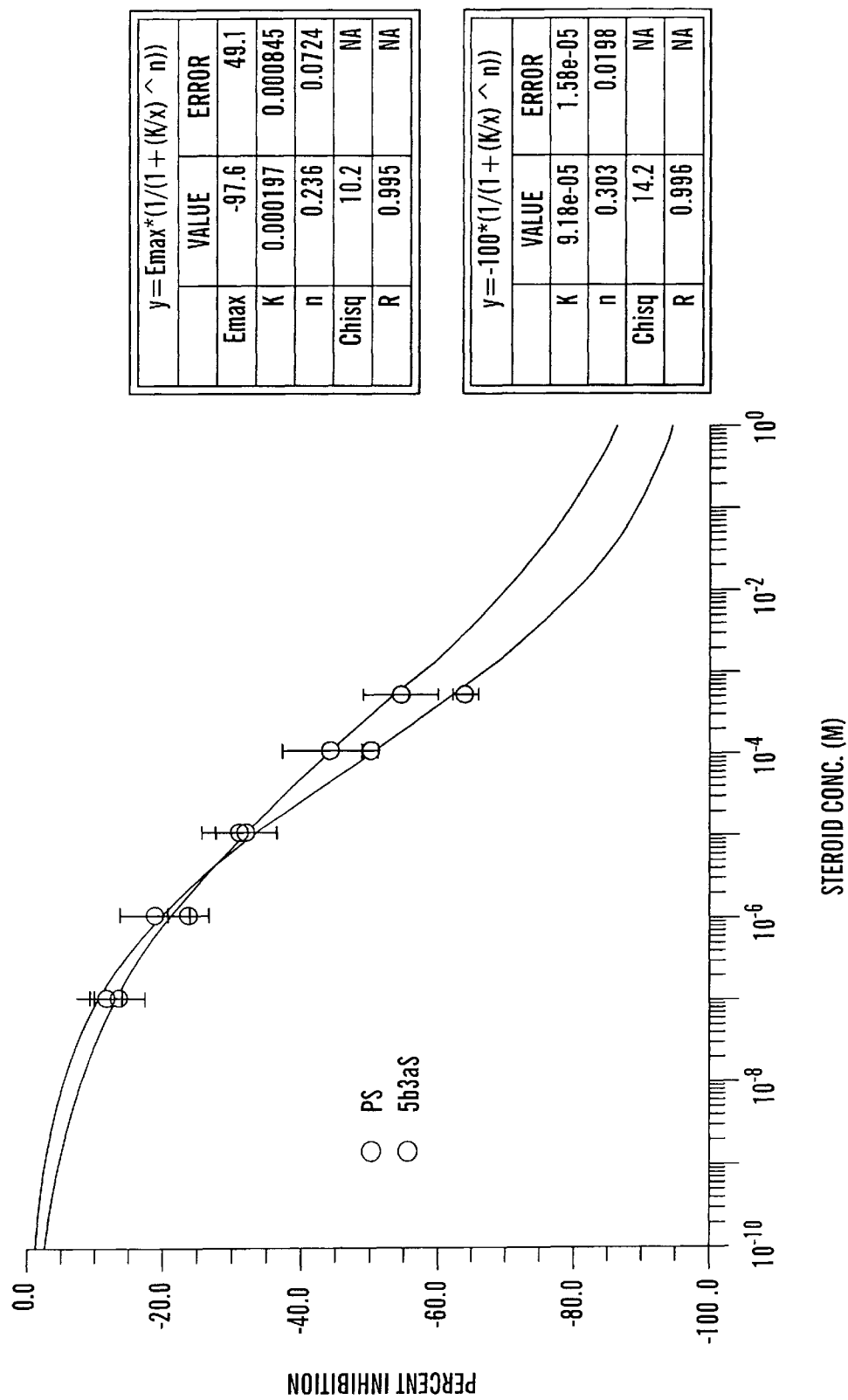
FIG. 12 depicts steroid IC50 determinations for recombinant GluR6 receptors.

FIG. 12 depicts steroid, pregnenolone sulfate and 5$\beta$3$\alpha$S, IC50 determined for recombinant GluR6 receptors under Vh of about $-100$ mV. Increasing concentrations of two steroids were applied with 10 $\mu$M kainate to determine the steroid IC50.

Figure 13:
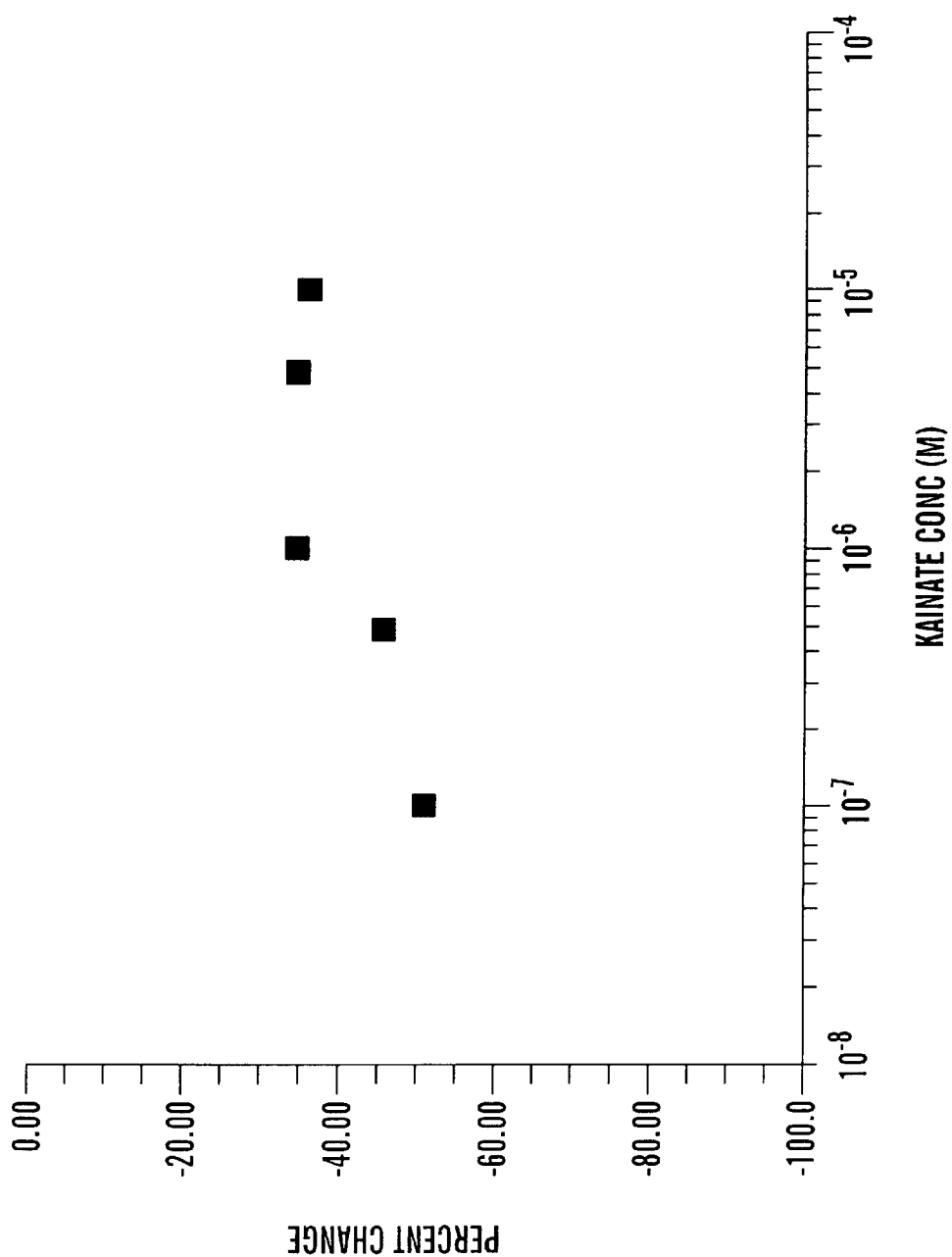
FIG. 13 depicts the kainate concentration dependence of pregnenolone sulfate inhibition.

FIG. 13 depicts the kainate concentration dependence of pregnenolone sulfate inhibition. To further characterize the mechanism of inhibition for neuroactive steroids, pregnenolone sulfate was applied with increasing concentrations of kainate to determine the percent inhibition observed. It was found that concentration dependence of 100 $\mu$M pregnenolone sulfate inhibition of kainate induced currents. The currents were expressed as percent change from kainate D-R. Percent change was calculated as $(I_{kain+PS}/I_{kain})-1) \cdot 100$.

Figure 14:
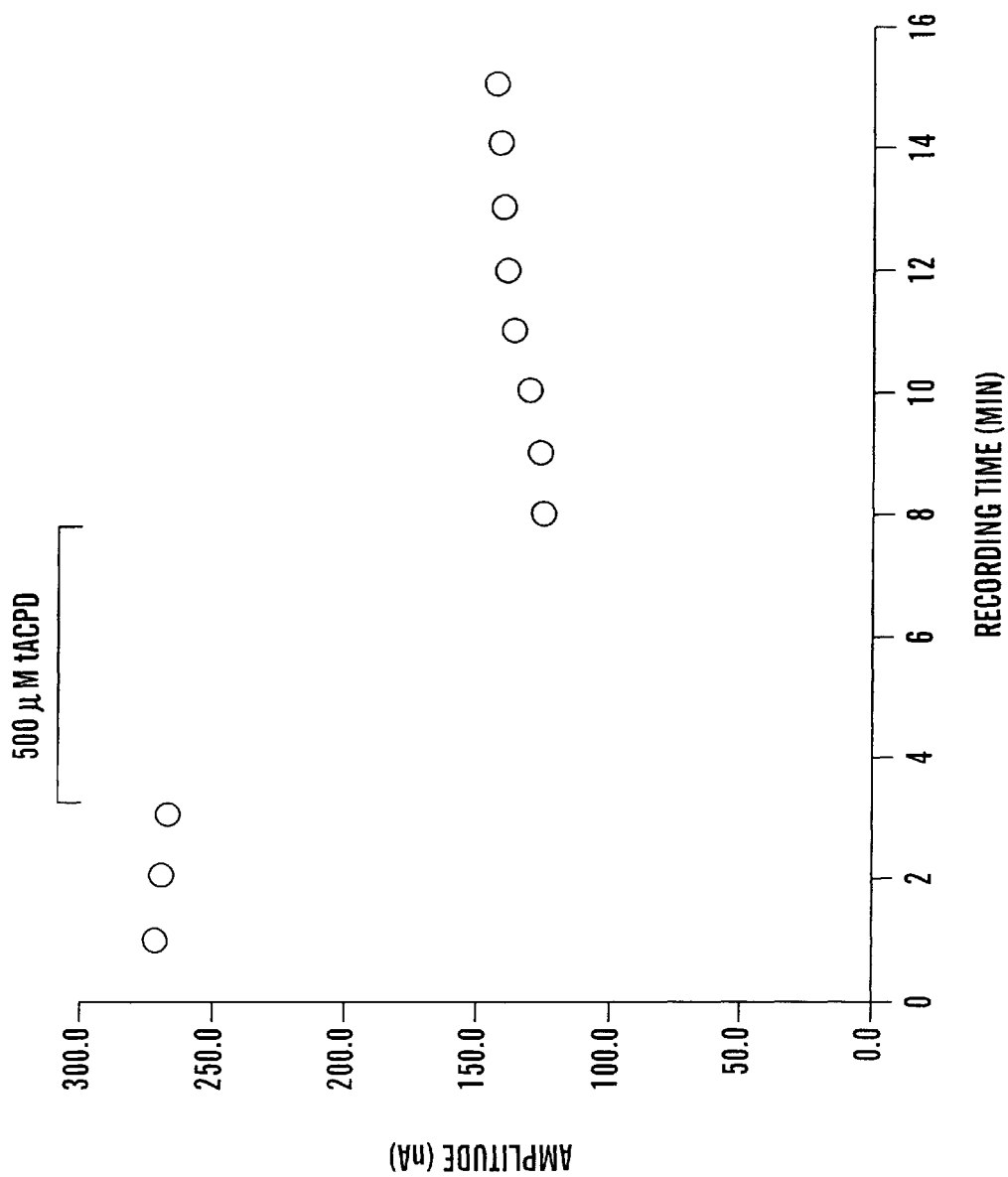
FIG. 14 depicts inhibition of kainate responses by stimulation of metabotropic glutamate receptors.

FIG. 14 depicts inhibition of kainate responses by stimulation of metabotropic glutamate receptors. The ability of a system according to the invention to do repetitive applications of agent solutions was used to make the finding that about 500 $\mu$M of the metabotropic agonist, tACPD, can inhibit responses to kainate of about 100 $\mu$M in oocytes injected with rat brain poly $A^+$ mRNA.

Detailed specification one implementation of the cellular physiology workstation is listed in Table 1.

TABLE 1

Parameters of perfusion system and recording chamber of a cellular physiology workstation

| Parameter | Measured value |
| --- | --- |
| rise time (5% to 95%) | about 70 msec to about 140 msec |
| solution exchange time (90%) | about 8 second |
| lag time | about 100 msec |
| flow rate | about 1.5 ml/minute to about 3.0 ml/minute |
| chamber volume | about 75 $\mu$l to about 100 $\mu$l |
| dead volume | about 1 $\mu$l |

Simultaneous Perfusion of Parallel Recording Chambers

The cellular physiology workstation may also be directed to simultaneous recordings from multiple oocytes such as, for example, simultaneous and coordinated perfusion of two or more recording chambers. Several approaches can be taken to accomplish this objective.

First, valve outputs can be divided into two or more channels using tubing leading into separate manifolds. Solution from each constant-flow chamber flow into a single valve, where it diverges into two or more channels. With this approach, only one set of solutions has to be made up prior to experimentation which reduces the problem of slight differences in concentration obtained from making up multiple, but distinct batches.

Second, the constant-flow chambers are manufactured with multiple output lines. Each output line feeds into a separate valve and, subsequently, into a separate manifold. This approach requires a greater expenditure in valves and associated control circuitry, but minimizes hydrodynamic problems associated with division of solution flow.

Lastly, separate sets of constant-flow chambers can be used for each recording chamber. Though easier to implement, this requires a greater daily expenditure of time required to prepare solutions as well as the expense of additional valves.

Electrophysiological recordings from Xenopus oocytes are typically performed using a voltage-clamp amplifier in two-electrode voltage-clamp mode. This method utilizes both a voltage-recording electrode and a current-injecting electrode for the control of membrane voltage. Electrophysiological recordings from additional oocytes may require two additional electrodes per oocyte, as well as appropriate headstages and micromanipulators for positioning of electrodes.

The present design of commercially available voltage-clamp amplifiers, however, only provides inputs for two microelectrode headstages. A multichannel amplifier for electrophysiology can be used to allow simultaneous recordings from multiple cells. Several approaches can be taken.

First, simultaneous recordings can be based on commercially available voltage-clamp amplifiers. One amplifier and two intracellular electrodes can be used with each recording chamber in a typical recording configuration. Electrophysiological traces are acquired from the multiple amplifiers using the currently existing data acquisition system, as described below, which has the capacity to capture up to 10 channels of analog data.

Low-cost amplifiers that have a smaller size and lack the extensive features found on higher cost amplifiers may also be used. Several of these amplifiers can be combined into a multi-channel device that readily handle simultaneous recordings. Electrophysiological traces from these separate amplifiers would feed into the currently existing data acquisition system.

Another embodiment incorporates an amplifier that is designed to handle multichannel data and facilitate simultaneous recordings. This device can have inputs for up to about 10, or more, microelectrode headstages and the appropriate circuitry for electrode zeroing, bridge balancing and adjustments for capacitative currents and series resistance. Designed from the outset as an amplifier for simultaneous recordings from multiple cells, this instrument is able to acquire multi-channel data at high speed and smoothly integrates into a fully automated system for simultaneous recordings.

Another embodiment is based on designing a novel instrument that accepts input from about 10 microelectrode headstages and feeds the data into standard, commercially available voltage clamp amplifiers. This device would have its own circuitry to maintain the proper holding potential for a given cell while the device is cycling through the other cells. This type of device eliminates the need and expense of purchasing multiple amplifiers.

One embodiment of the invention utilizes the MacADIOS II board by GW Instruments, Inc., for data acquisition and instrument control. This NuBus-based board is configured with two analog-to-digital converters (ADC) that can acquire 2-channel data at about 25 KHz, but is also capable of multiplexed data acquisition of about 10 or more channels at about 3 KHz, which is of sufficient resolution for Xenopus oocyte electrophysiology. Thus, the design of the automated workstation for electrophysiology enables simple scale-up which may not require additional computer or data acquisition boards. Electrophysiological traces from the additional recording chambers would be either displayed in separate windows or superimposed for independent viewing and analysis.

An application of a cellular physiology workstation with highly parallel monitoring and perfusion capabilities is the rapid generation of dose-response data from multiple oocytes. A series of agent solutions of increasing concentration can be prepared in the constant-flow chambers of the perfusion system and the lines and manifold primed to load an agent to be tested. By sweeping the microscope head across the stage of parallel recording chambers, RNA-injected oocytes are successively positioned in each recording chamber and impaled with both voltage-recording and current-injecting microelectrodes. Electrode zeroing, bridge balancing, and adjustments for capacitative currents and series resistance are each independently performed as required on each voltage-clamp amplifier. For a typical dose-response experiment, multiple voltage-clamp amplifiers are simultaneously stepped to a holding potential appropriate for the ionic current under study. This can be accomplished by distributing the output of the digital-to-analog converter (DAC) from the MacADIOS II board to the separate voltage-clamp amplifiers. The perfusion system may be set to deliver the desired agent solutions to the multiple recording chambers simultaneously. Depending upon experimental design, multiple oocytes may be simultaneously exposed to the same agent to replicated a single experiment on multiple oocytes, or ech oocyte can be exposed to a different agent to facilitate rapid screening of large drug libraries. Current and voltage recordings are acquired from each amplifier and fed into appropriate windows in the SuperScope II virtual instrument. At the conclusion of the protocol, automated routines perform waveform analysis on each current recording.

While the automated electrophysiological workstation is particularly suited to oocyte electrophysiology, the approach described in general can be readily adapted to patch-clamp electrophysiology, calcium imaging studies, confocal microscopy and other applications where perfusion control and data acquisition need to be tightly integrated. Any type of biosensor capable of producing an electrical output, such as a sensor capable of measuring concentrations of substances within the cell, can be used in place of or in addition to the voltage-measuring electrode. Biosensors are well known to those of skill in the art and are reviewed for example by Lowe (Lowe, C. R. Biosensors, Trends in Biotechnology, 2:59–65, 1984) and by Byfield and Abuknesha (Byfield, M. P., Abuknesha, R. A. Biosensors & Bioelectronics 9:373–400 1994). Other automation aspects that may be optionally incorporated into the automated cellular physiology workstation are digitally controlled voltage-clamp amplifiers, and robotics and machine vision to automate the tasks of oocyte placement and microelectrode positioning to result in a fully automated electrophysiological assay system.

Other embodiments and uses of the invention will be apparent to those skilled in the art from consideration of the specification and practice of the invention disclosed herein. All references cited herein, for whatever reason, are specifically incorporated by reference. The specification and examples should be considered exemplary only with the true scope and spirit of the invention indicated by the following claims.

EXAMPLES

Example 1

Oocyte Isolation

Female, oocyte positive *Xenopus laevis* frogs, purchased from Nasco, Inc. were kept on an about 12 hour light/about 12 hour dark cycle. Frogs were maintained on a diet of chopped calf liver fed about every three days. Prior to surgery, frogs were anesthetized in a solution containing about 0.15% Tricaine for about 30 minutes. Ovarian sections were removed through a lateral abdominal incision, after which the incision was sutured with about 4 to about 5 stitches and the animal allowed to recover in isolation for about 3 hours to about 4 hours. Ovarian lobules containing follicular oocytes were immediately placed in calcium-free ND96 solution (96 mM NaCl, 1 mM $MgCl_2$, 2 mM KCl, 50 mM Hepes, 2.5 mM pyruvate) and cut into groups of about 10 to about 20 oocytes. Following a treatment with collagenase (Sigma, type II, 2 mg/ml) at about 2 mg/ml for about 2 hours at room temperature, individual oocytes were obtained free of their follicular layer. Selected Dumont stage V and VI oocytes were then transferred to 60×15 mm glass petri dishes containing ND96 (96 mM NaCl, 1 mM $MgCl_2$, 2 mM KCl, 50 mM Hepes, 2.5 mM pyruvate) and maintained in an incubator at about 18° C. to about 20° C. On the following day, batches of about 20 oocytes to about 30 oocytes were injected with about 30 nl to about 80 nl prepared RNA solution using an electronic microinjector (Drummond Instruments, Inc.).

Example 2

RNA Preparation

RNA was prepared for injection into oocytes by extraction of mRNA from brain tissue and by synthesis using in vitro transcription of linearized DNA templates encoding recombinant receptor subunits.

The extraction technique of RNA preparation uses brain mRNA from chick embryos of about 19 day old as staring material. Extraction was performed using the Dynabeads Oligo-$dT_{(25)}$ isolation kit (Dynal, Inc.) which utilizes magnetic beads having an attached polythymidine oligomer to allow magnetic separation of poly$(A)^+$ RNA from cell homogenates.

In vitro transcription was performed using plasmids containing the GluR3 (flop) and GluR6 cDNA as starting material. Plasmids were linearized with restriction endonuclease XhoI (GluR3) or XbaI (GluR6) prior to in vitro transcription with T3 RNA polymerase using a commercially available kit (Message Machine; Ambion, Inc.; Austin, Tex.).

Example 3

Electrophysiology

About 3 days to about 5 days after RNA injection, electrophysiological recordings were carried out using an Axoclamp-2A voltage clamp amplifier (Axon Instruments, Inc.). Experiments were performed in two-electrode voltage clamp mode using two intracellular microelectrodes of about 1 to about 3 mega-ohm resistance filled with a solution of about 3M KCl. A close-up view of an oocyte under impalement in voltage-clamp mode is shown in FIG. 7.

Oocytes were usually clamped at a holding potential of about 40 mV and stepped to about −100 mV during agent application. GluR6 injected oocytes were treated for about 10 minutes with a solution of about 10 μg/ml concanavalin A to prevent fast desensitization of kainate responses.

Example 4

Application of GABA to Oocytes

In this experiment, a solution comprising about 100 μM GABA was applied to an oocyte expressing $GABA_A$ receptors to test the function of the automated workstation. Oocytes were immobilized in the recording chamber, impaled with voltage-recording and current-injecting microelectrodes, and allowed about one to about two minutes to recover to a resting membrane potential of about 40 mV to about −50 mV. The amplifier was switched into voltage clamp mode, typically at a holding potential of about −60 mV, prior to the start of experimentation protocol.

A typical experimental protocol may comprise the steps of prepulse, agent application, and washout phases and the function of each phase may be set up in advance by defining the positions of on-screen markers M1–M4, which can be easily moved via a user input device such as a computer mouse. The PREPULSE VALVE selector is used to select a prepulse solution which may be used to pre-equilibrate with a modulator before coapplication of modulator and agonist. The modulator is applied during the interval M1 to M2. The DRUG VALVE panel of buttons is next used to select the solution that is to be applied during the interval M2 to M3. Finally, the WASH VALVE selector is used to select the solution to be applied during the washout phase of the protocol, defined as the interval M3 to M4. The WASH VALVE selector also controls the WASH TIMER, which perfuses the oocyte for a preset amount of time between successive episodes.

After the perfusion controls were set, the VC COMMAND slider is used to select the voltage offset that will be sent to the amplifier to determine the holding potential at the start of the first episodes. The oocytes were held at about −60 mV and stepped to about −100 mV at the start of data acquisition to increase electrochemical driving forces; this entails a voltage offset being sent to the amplifier of about 40 mV. Experiments usually consist of multiple episodes per trial, where an episode is defined as a single cycle of data acquisition. The EPISODES PER TRIAL selector is used to select the number of episodes to be acquired, after which the experiment is started by pressing the BEGIN button. At the initiation of data acquisition, the holding potential is stepped to the preset voltage, and perfusion commences with the selected solutions. At the end of data acquisition, the current and voltage traces were saved to disk, and the oocyte is perfused with wash solution for a predetermined amount of time. Each episode is logged to the journal window, where analysis routines measure and log waveform parameters. From this basic protocol more complex protocols were developed that automatically execute repetitive application, dose-response, reversal potential and voltage-stepping experiments.

Example 5

Repetitive Application Experiments

Figure 15A:
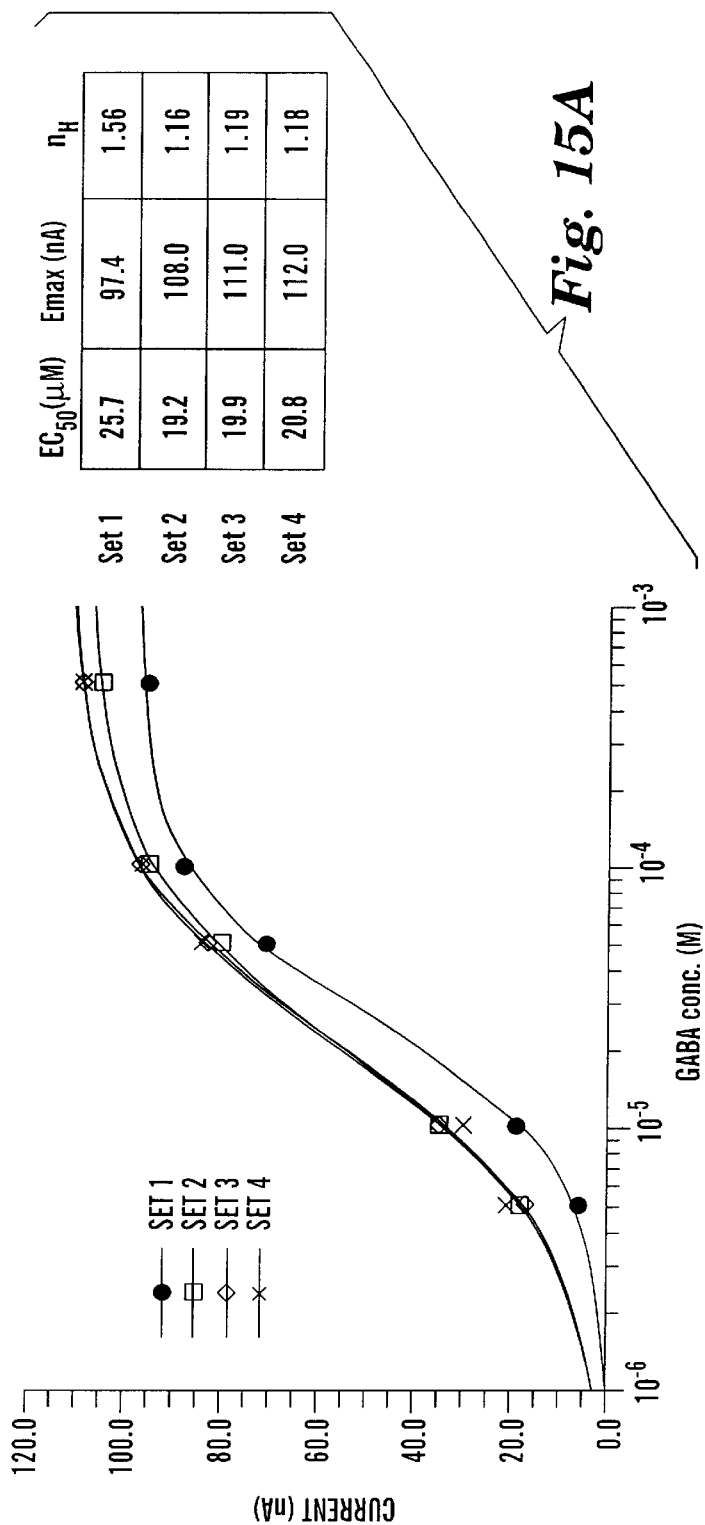
FIG. 15 depicts γ-aminobutyric acid (GABA) dose-response curves revealing reproducibility of GABA $EC_{50}$.
Figure 15B:
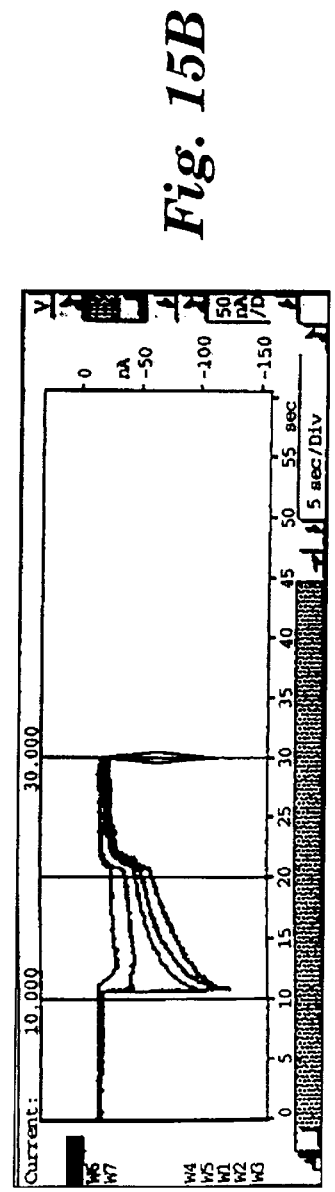

The EPISODES PER TRIAL selector is used to specify a repetitive application protocol in which multiple cycles of agent application are desired. FIG. 15 shows the results from an experiment in which 100 μM GABA was applied repeatedly to an oocyte injected with chick brain poly$(A)^+$ RNA. A protocol of about 30 seconds was used, consisting of a 10 second prepulse with buffer solution, a 10 second application of 100 μM GABA, and a wash phase of about 10 seconds, followed by a wash cycle of about 60 seconds with buffer solution prior to the next application of agent. An increase in current amplitude was evident that reached a plateau over the course of about one hour experiment in which 100 μM GABA was applied 30 times. These experiments demonstrate the utility of the workstation that has been developed, as the experiment is performed automatically without any operator intervention. This type of protocol is useful for following a response over an extended period of time which is useful for looking at time-dependent processes such as rundown of receptor mediated responses.

This protocol can also be used to study the effects of compounds that have a slow time course of action, for example, compounds that affect the phosphorylation state of receptors, such as kinase inhibitors or membrane permeant cAMP analogues. Lastly, the repetitive application feature makes it possible to easily compare averaged data taken before and after an experimental manipulation. By avoiding comparison between single responses, averaging of data reduces errors due to response variability, noise and time-dependent changes in response amplitude.

Example 6

Dose-Response Determination

An automated workstation for electrophysiology was designed to filly automate dose-response experimentation. Typically, the generation of dose-response data is usually achieved by application of increasing concentrations of a given agent to a responsive cell. FIG. 8 shows the results of a dose-response experiment in which increasing concentrations of kainate were applied to an oocyte expressing homomeric GluR3 kainate receptors formed from cloned receptor subunits. For the kainate response from this cell an $EC_{50}$ of about 27 $\mu$M was calculated. This type of experiment is initiated by pressing the DOSE/RESPONSE button which selects a protocol designed to sequentially step through a series of agent solutions, beginning at the valve specified by the ALTERNATE VALVE selector. The EPISODES PER TRIAL selector is then used to specify 12 episodes, corresponding to the number of concentrations to be tested. The dose-response protocol closely follows the operation of the repetitive application protocol, with the exception that this protocol increments the DRUG VALVE selection after each episode.

Figure 16:
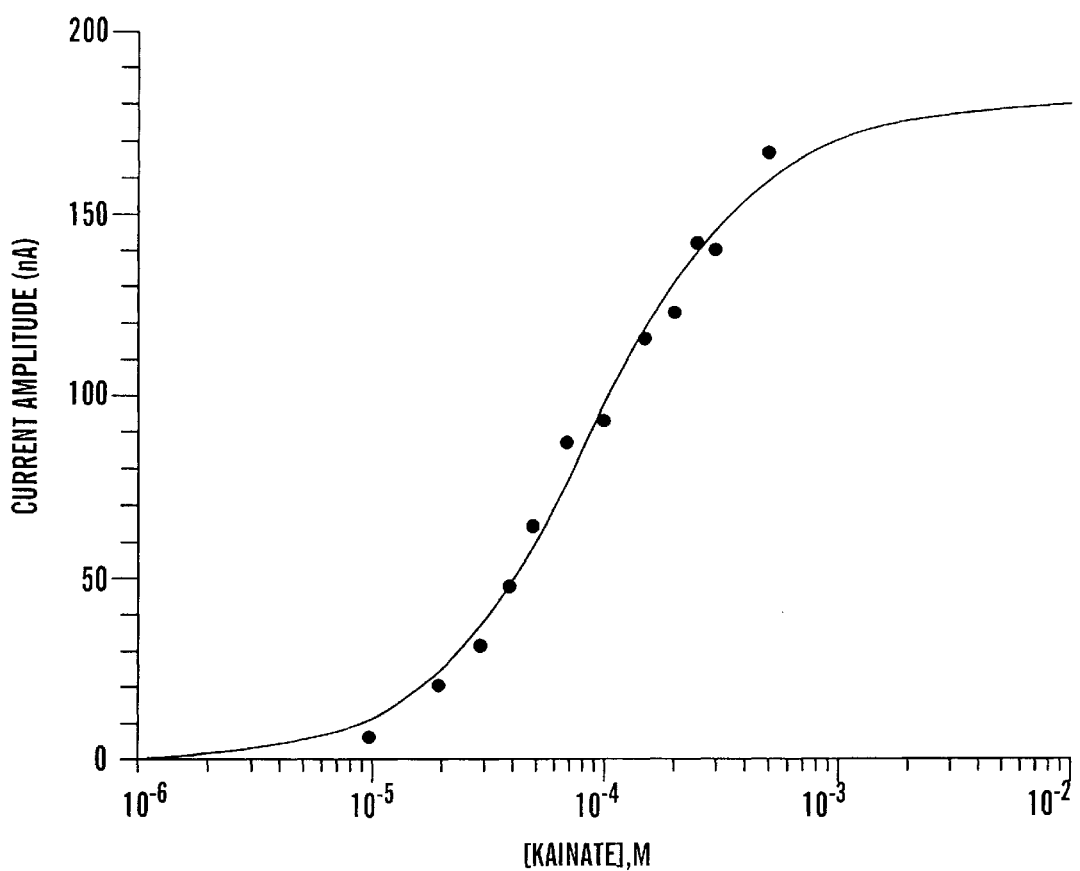
FIG. 16 depicts a high-resolution dose-response curve generated by the cellular physiology workstation.

FIG. 16 shows a high-resolution dose-response curve generated by the Cellular physiology workstation. In this experiment, increasing concentrations of kainate are sequentially applied to an oocyte expressing rat GluR3 receptors. An automated protocol steps through up to about 15 different agent concentrations to rapidly generate dose-response curves. An $EC_{50}$ of about 90 $\mu$M was determined for GluR3 receptors expressed in Xenopus oocytes. Oocyte was held at about -100 mV during kainate application and washed for about 60 seconds between episodes. Total duration of this experiment, which was performed automatically without operator intervention, was about 15 minutes.

FIG. 15 depicts the reproducibility of dose-response curves generated by the cellular physiology workstation. Four separate GABA dose-response determinations were made about 20 minute apart to document system performance. $EC_{50}$ determinations yielded similar results (26 $\mu$M, 19 $\mu$M, 20 $\mu$M, and 21 $\mu$M) over the course of this 70 minute experiment. Oocytes were held at about -100 mV during application of about 5 $\mu$M, about 10 $\mu$M, about 50 $\mu$M, about 100 $\mu$M and about 500 $\mu$M GABA, and washed for about 30 seconds between episodes. Dose-response curves were determined on an oocyte expressing $GABA_A$ receptors after injection with chick brain poly $A^+$ RNA.

Figure 17:
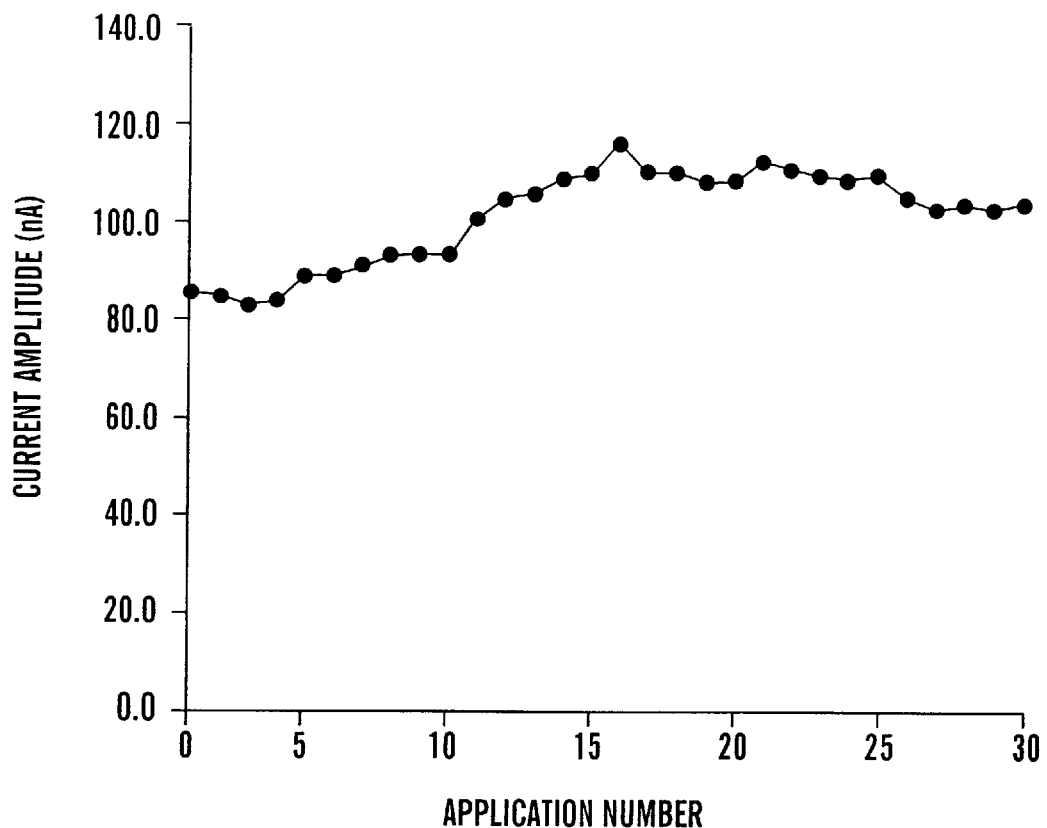
FIG. 17 depicts current responses to 30 consecutive applications of 100 $\mu$M GABA.

In a separate experiment, to determine reproducibility and reliability of agonist responses, the cellular physiology workstation was used to determine current responses to 30 consecutive applications of 100 $\mu$M GABA (FIG. 17). Current responses to 30 consecutive applications of 100 $\mu$M GABA are shown in an oocyte expressing $GABA_A$ receptors after injection with chick brain poly $A^+$ RNA. Slight increases in current amplitude are observed during the course of this 45 minute experiment, which was performed automatically without operator intervention. Oocytes were held at about -100 mV during agent application and washed for about 1 minute with Ringer solution between each of the 30 episodes.

Example 7

Reversal Potential Determination

Figure 18:
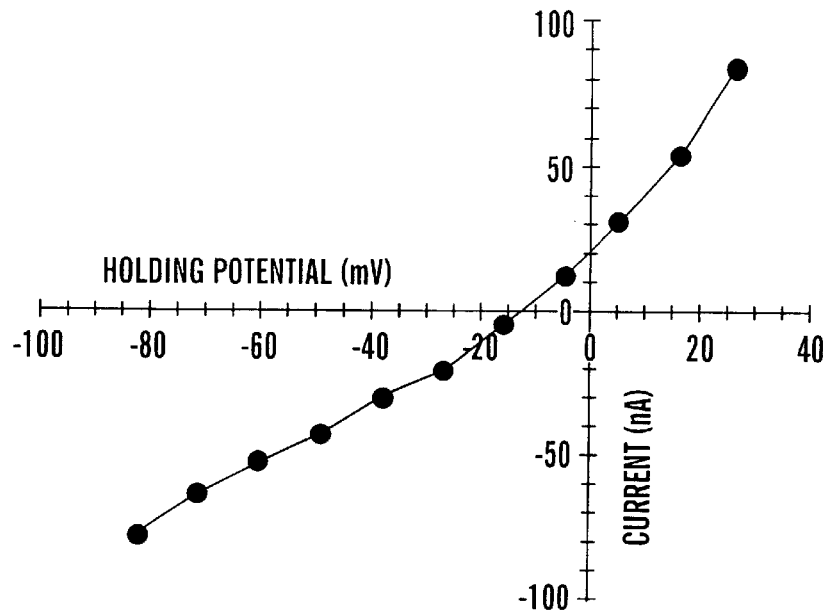
FIG. 18 depicts determination of reversal potential generated automatically by the cellular physiology workstation.

The virtual instrumentation that was developed also provides control over the voltage-clamp amplifier, thereby making it possible to automate experiments in which holding potential may be varied, such as those determining reversal potentials and examining current-voltage relationships. A reversal potential for a receptor-mediated response is the voltage at which no net current is observed upon activation of the ionic conductances associated with the receptor. Reversal potentials are typically determined by applying a given agent at various holding potentials, plotting current vs. holding potential, and calculating the voltage at which the current reverses direction. FIG. 18 shows the results of an experiment in which a reversal potential of about -15 mV to about -10 mV was determined for the kainate response in oocytes expressing GluR6 kainate receptors. The holding potential was progressively increased from about -80 mV to about +25 mV in 11 steps of about 10 mV. The oocyte was returned to a holding potential of -60 mV and washed for about 30 second after each agent application. The direction of the kainate-induced current was found to reverse between about -is mV and about -10 mV. This type of automated protocol can also be used to determine current-voltage relationships, in the absence and presence of a receptor modulator and to investigate mechanisms of action of modulatory drugs. For these types of voltage experiments, the STEP SIZE slider is used with a multi-episode trial to increment the VC COMMAND offset, which controls the holding potential of the amplifier.

Example 8

Voltage-Stepping Response

Figure 19A:
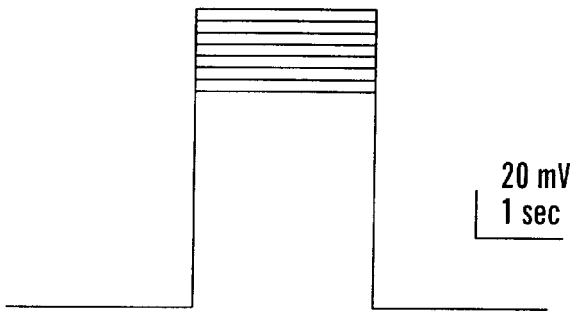
FIG. 19 depicts an examination of the endogenous calcium-dependent chloride current ($I_{Cl^-(Ca)}$) present in native oocytes.
Figure 19B:
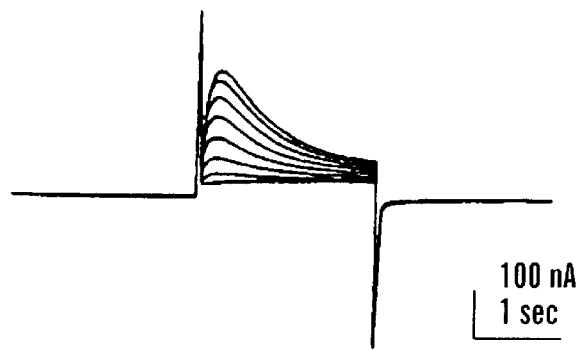

The examples described above used a perfusion system for applying a receptor ligand during the period between the M2 and M3 markers to generate a receptor-mediated response. The cellular physiology workstation may also be programmed for examining voltage-gated ion channels. For example, the Xenopus oocyte membrane has a number of well characterized voltage-dependent conductances, including an endogenous chloride current ($I_{Cl^-}$), an endogenous calcium-dependent chloride current ($I_{Cl^-(Ca++)}$), and an endogenous sodium current ($I_{Na+}$), that can sometimes interfere with other currents of interest and may sometimes be subtracted out. FIG. 19 shows traces from an experiment using the cellular physiology workstation to examine endogenous, calcium-dependent chloride current ($I_{Cl^-(Ca++)}$) found in native Xenopus oocytes. Voltage was stepped from about -100 mV to about +20 mV, each time returning to a holding potential of about -60 mV, to determine the current-voltage relationship for this conductance. In these types of experiments, voltage is stepped from thy amplifier's holding potential to a voltage determined by the VC COMMAND and STEP SIZE sliders during the M2–M3 interval. Predefined protocols are in this way established for voltage-dependent conductances of interest, and can be easily selected through on-screen buttons. This type of protocol can be used to screen recombinant voltage-dependent ion channels against libraries of agents such as drug libraries.

Other embodiments and uses of the invention will be apparent to those skilled in the art from consideration of the specification and practice of the invention disclosed herein. All references cited herein, for whatever reason, are specifically incorporated by reference. The specification and examples should be considered exemplary only with the true scope and spirit of the invention indicated by the following claims.

```
****************************************************************************
INSTRUMENT * INSTRUMENT * INSTRUMENT * INSTRUMENT * INSTRUMENT * INSTRUMENT
Name: oocyte.77
Application: SuperScope II
Version: 1.43 (68k)
****************************************************************************
DIGITIZER * DIGITIZER * DIGITIZER * DIGITIZER * DIGITIZER * DIGITIZER * DIGITIZER
Digitizer: MacADIOS II
Driver: Inout
Data Collection Mode: Chart
Trigger Mode: none
Timebase: 600 pts/trace, 100.00 pts/sec
****************************************************************************
DISPLAYS * DISPLAYS * DISPLAYS * DISPLAYS * DISPLAYS * DISPLAYS * DISPLAYS
Display Name
*************
Current
Voltage
****************************************************************************
MARKERS * MARKERS * MARKERS * MARKERS * MARKERS * MARKERS * MARKERS
Marker Name
*************
M1
M2
M3
M4
****************************************************************************
JOURNALS * JOURNALS * JOURNALS * JOURNALS * JOURNALS * JOURNALS * JOURNALS
Journal Name
*************
Journal 1
jHeader
****************************************************************************
STRINGS * STRINGS * STRINGS * STRINGS * STRINGS * STRINGS * STRINGS * STRINGS
Name         Units  Text
****************************************************************************
retValue     Volts  7
message      Volts  2.12
sAmplitu     Volts  670 nA
sVwash       Volts  0 /
sTrace       Volts  Trace # 128
sVdrug       Volts
sTime        Volts  at 16:04:32
sVwash2      Volts  0
sVoffset     Volts  Vh offset = 120 mV
sM2          Volts  M2 = 2.0
sM3          Volts  ,M3 = 4.0
sM4          Volts  ,M4 = 6.0
sWash        Volts  Wash 0 sec
SAbort       Volts
_SaveWav     Volts  8/29/95.AD1.128
_LoadWav     Volts  8/29/95.AD1.103
S15          Volts
sMax         Volts  309.6 nA at 4.03 s
wTmax        sec    4.03
****************************************************************************
WAVES * WAVES * WAVES * WAVES * WAVES * WAVES * WAVES * WAVES * WAVES * WAVES
Wave Name   Wave Type   V Units   H Units   Length   ValidPts
****************************************************************************
AD0         Integer     Volt      sec       0        0
AD1         Integer     A         sec       0        0
Dout        Integer     Volt      sec       0        0
seg2.4      Integer     A         sec       0        0
DA0         Integer     Volt      sec       0        0
Selected    Float       Volt      sec       0        0
Flip        Float       A         sec       0        0
Dseg2.3     Integer     Volt      sec       0        0
W1          Integer     A         sec       0        0
W2          Integer     A         sec       0        0
W3          Integer     A         sec       0        0
W4          Integer     A         sec       0        0
W5          Integer     A         sec       0        0
W6          Integer     A         sec       0        0
```

| | | | | | |
|---|---|---|---|---|---|
| W7 | Integer | A | sec | 0 | 0 |
| seg3.4 | Float | A | sec | 0 | 0 |
| Vseg2.3 | Integer | Volt | sec | 0 | 0 |

* Wave End Points *

| Wave Name | 1st Point H Value | Last Point H Value | Sample Period |
|---|---|---|---|
| AD0 | 0.000000 | −0.01000 | 0.010000 |
| AD1 | 0.000000 | −0.01000 | 0.010000 |
| Dout | 0.000000 | −0.01000 | 0.010000 |
| seg2.4 | −0.010000 | −0.02000 | 0.010000 |
| DA0 | 0.000000 | −0.01000 | 0.010000 |
| Selected | 17.279999 | 17.278999 | 0.001000 |
| Flip | 2.010000 | 2.00000 | 0.010000 |
| Dseg2.3 | −0.01000 | −0.02000 | 0.010000 |
| W1 | 0.000000 | −0.01000 | 0.010000 |
| W2 | 0.000000 | −0.01000 | 0.010000 |
| W3 | 0.000000 | −0.01000 | 0.010000 |
| W4 | 0.000000 | −0.01000 | 0.010000 |
| W5 | 0.000000 | −0.01000 | 0.010000 |
| W6 | 0.000000 | −0.01000 | 0.010000 |
| W7 | 0.000000 | −0.01000 | 0.010000 |
| seg3.4 | 2.000000 | 1.990000 | 0.010000 |
| Vseg2.3 | −0.01000 | −0.02000 | 0.010000 |

* Wave Mapping For 16 bit Integer Waves *

| Wave Name | Quanta | Min Code | Max Code | Min Value | Max Value |
|---|---|---|---|---|---|
| AD0 | 0.000488 | −2048 | 2047 | −1.000000 | 0.999512 |
| AD1 | 0.000000 | 0 | 4095 | −0.000001 | 0.000001 |
| Dout | 1.000000 | −32768 | 32767 | −32768.000000 | 32767.000000 |
| seg2.4 | 0.000000 | 0 | 4095 | −0.000001 | 0.000001 |
| DA0 | 0.004883 | −2 048 | 2048 | −10.000000 | 10.000000 |
| Dseg2.3 | 1.000000 | −32768 | 32767 | −32768.000000 | 32767.000000 |
| W1 | 0.000000 | 0 | 4095 | −0.000001 | 0.000001 |
| W2 | 0.000000 | 0 | 4095 | −0.000001 | 0.000001 |
| W3 | 0.000000 | 0 | 4095 | −0.000001 | 0.000001 |
| W4 | 0.000000 | 0 | 4095 | −0.000001 | 0.000001 |
| W5 | 0.000000 | 0 | 4095 | −0.000001 | 0.000001 |
| W6 | 0.000000 | 0 | 4095 | −0.000001 | 0.000001 |
| W7 | 0.000000 | 0 | 4095 | −0.000001 | 0.000001 |
| Vseg2.3 | 0.004883 | −2048 | 2048 | −10.000000 | 10.000000 |

* Segments *

| Segment | Parant | M1 Name | M2 Name | M1 Time | M2 Time |
|---|---|---|---|---|---|
| seg2.4 | AD1 | M2 | M4 | 10.000000 | 30.000000 |
| Dseg2.3 | Dout | M2 | M3 | 10.000000 | 20.000000 |
| seg3.4 | Flip | M3 | M4 | 20.000000 | 30.000000 |
| Vseg2.3 | DA0 | M2 | M3 | 10.000000 | 20.000000 |

* First 5 Points *

| Wave Name | Point #1 | Point #2 | Point #3 | Point #4 | Point #5 |
|---|---|---|---|---|---|
| AD0 | | | | | |
| AD1 | | | | | |
| Dout | | | | | |
| seg2.4 | | | | | |
| DA0 | | | | | |
| Selected | | | | | |
| Flip | | | | | |
| Dseg2.3 | | | | | |
| W1 | | | | | |
| W2 | | | | | |
| W3 | | | | | |
| W4 | | | | | |
| W5 | | | | | |
| W6 | | | | | |
| W7 | | | | | |
| seg3.4 | | | | | |
| Vseg2.3 | | | | | |

VARIABLES * VARIABLES * VARIABLES * VARIABLES * VARIABLES * VARIABLES

| Name | Units | Value |
|---|---|---|
| error | Volts | 1.0000001 |
| V1 | Volts | 10.000000 |
| V2 | Volts | 0.000000 |
| V3 | Volts | 0.000000 |
| V4 | Volts | 0.000000 |
| val.dio | Volts | 145.000000 |
| Dout | | 1.000000 |
| Dport | | 0.000000 |

-continued

| | | |
|---|---|---|
| n0 | Volts | 0.000000 |
| n1 | Volts | 0.000000 |
| n2 | Volts | 0.000000 |
| n3 | Volts | 0.000000 |
| n4 | Volts | 0.000000 |
| n5 | Volts | 0.000000 |
| n6 | Volts | 0.000000 |
| n7 | Volts | 0.000000 |
| n8 | Volts | 0.000000 |
| n9 | Volts | 0.000000 |
| n10 | Volts | 0.000000 |
| n11 | Volts | 0.000000 |
| n12 | Volts | 0.000000 |
| n13 | Volts | 0.000000 |
| n14 | Volts | 0.000000 |
| n15 | Volts | 0.000000 |
| secs | Volts | 0.000000 |
| cnt1 | Volts | 0.000000 |
| Vwash | Volts | 1.000000 |
| WashOut | Volts | −2.000000 |
| cnt2 | Volts | 4.000000 |
| vOut | Volts | 0.000000 |
| Marker4 | Volts | 30.000000 |
| _Tracesi | Volts | 2999.999756 |
| _SampleP | Volts | 0.010000 |
| vVCstep | Volts | 40.000000 |
| NewDAC | Volts | 140.000000 |
| selected | Volts | 1.000000 |
| cnt3 | Volts | 5.000000 |
| timeV | Volts | 0.400000 |
| V39 | Volts | 0.000000 |
| V40 | Volts | 6.000000 |
| V41 | Volts | 24.000000 |
| wMax | A | 300.570312 |
| wMin | A | −360.839844 |
| wAmplitu | A | 670.410156 |
| tracenum | Volts | 0.000000 |
| Marker3 | Volts | 4.000000 |
| Marker2 | Volts | 2.000000 |
| vDelSeg | Volts | 5.930000 |
| previous | Volts | 0.000000 |
| V50 | Volts | 0.903090 |
| V51 | Volts | 0.301030 |
| cnt4 | Volts | 3.000000 |
| flushlp | Volts | 4.000000 |
| Vflush | Volts | 16.000000 |
| FlushOut | Volts | −17.000000 |
| loadloop | Volts | 7.000000 |
| V57 | Volts | 103.000000 |
| V58 | Volts | 7.000000 |
| V59 | Volts | 109.000000 |
| vVCcom | Volts | 100.000000 |

\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*[001b]\*\*\*\*\*\*\*\*\*\*\*\*\*\*\*\*\*\*\*\*\*\*\*\*\*\*\*\*\*\*\*\*\*\*\*\*
DATAPIPES * DATAPIPES * DATAPIPES * DATAPIPES * DATAPIPES * DATAPIPES * DATAPIPES
Name     Pathname
\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*
Datapipe   Mac IIci 80HD:Technical:SuperScope II:Data:8/29/95:
Name     FileName   VolumeName    DirID     vRefNum   WDRef
\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*
Datapipe   .AD1.103   Mac IIci 80HD   145109       −1    −32477
\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*
TASKS * TASKS * TASKS * TASKS * TASKS * TASKS * TASKS * TASKS * TASKS * TASKS * TASKS
\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*\*

Task:wash                                          Allow mouse activity
Task Begin
String sAbort = "" appended onto end of string""
Variable WashOut = Variable Vwash + 1.000
Variable WashOut = Variable WashOut * −1.00
If(Control bpurge = 1.000) then ...
  Jump to subroutine "synth"
  Variable WashOut = Variable WashOut * −1.00
  If end
If(Control bHold = 0.00000) then ...
  Cwrite (devType147, offset=192, slot=4; WashOut to Value)
  If end
Variable secs = Control cWashtim * 60.00
Control iTimer .1 = 0.00000
While (Control iTimer .1 < Variable secs) do ...
  Synchronize to 1.00000 second intervals -continued

```
    Control iTimer .1 = Control iTimer .1 + 1.000
  While end
Cwrite (devTye147, offset=192, slot=4; -1.00 to Value)
Beep
If(Control bPurge = 0.00000) then
  String sWash = "Variable secs" insert into "Wash sec" after char 5 (base 1)
  String sWash = "String sAbort appended onto end of string "String sWash"
  Append text onto the end of Journal1 with data from string sWash
  Insert "
"into journal Journal1
  Insert"
"into journal Journal1
  If end
Control bPurge = 0.00000
************************************************************************
Task:abort                                                      Allow mouse activity
Task Begin
String sAbort = "Control iTimer.1" insert into "aborted at sec" after char 11
Control iTimer.1 = Variable secs
Variable cnt2 = Control dEpiNum
Break out of Trace loop
************************************************************************
Task:acquire                                                    Allow mouse activity
Task Begin
Variable cnt2 = 0.00000
Variable vVCcom = Control cVCcom
Jump to subroutine "duration"
Jump to subroutine "header"
Trace Loop Begin (30 traces)
  Control epicnt = Variable cnt2 + 1.000
  Jump to subroutine "synth"
  Variable tracenum = Variable tracenum + 1.000
  Digitize Trace (600 pts/trace, 100.00 pts/sec)
  Jump to subroutine "smooth"
  If(Control bAutosav = 0.00000) then ...
    Jump to subroutine "save"
    If end
  Jump to subroutine "analyze"
  Variable vOut = 0.00000
  Analog & Digital I/O (vOut to Aout0)
  Control bWash = 1.000
  Jump to subroutine "wash"
  Control bWash = 0.00000
  Variable cnt2 = Variable cnt2 + 1.000
  If(Control cVCstep != 0.00000) then ...
    If(Control dEpiNum > 1.000) then ...
      Variable vVCStep = Variable cnt2 * Control cVCstep
      Variable NewDAC = Variable vVCcom + Variable vVCstep
      Variable vOut = Variable NewDAC / 20.00
      Control cVCcom = Control cVCcom + Control cVCstep
      Fill wave 'DA0' with 0.00000, 24000 points
      If(Control bMarkers == 1.000) then ...
        Vseg2.3 = Vseg2.3 + variable vOut
        If end
      If(Control bMarkers == 0.00000) then ...
        DA0 = DA0 + variable vOut
        If end
      If end
    If end
  If variable cnt2 >= Control dEpiNum) then ...
    Variable vOut = 0.00000
    Analog & Digital I/O (vOut to Aout0)
    Break out of Trace Loop
    If end
  Clear & Update
  Trace Loop End
Cwrite(devType147, offset=192, slot=4; -1.00 to Value)
Control epicnt = 1.000
Jump to subroutine "footer"
************************************************************************
Task:synth                                                      Allow mouse activity
Task Begin
Fill wave 'AD0' with 0.00000, 24000 points
Fill wave 'AD1' with 0.00000, 24000 points
If(Control bDMD == 1.000) then ...
  If(Variable cnt2 == 2.000) then ...
    Variable V50 = Log10(Variable previous)
    Variable V51 = Log10(2.000)
    Variable selected = Variable V50/(Variable V51
```

-continued

```
      Variable selected = Int(Variable selected)
      Jump to subroutine "ButonSet"
      If end
   If end
Variable n0 = Control V0 * 1.000
Variable n1 = Control V1 * 2.000
Variable n2 = Control V2 * 4.000
Variable n3 = Control V3 * 8.000
Variable n4 = Control V4 * 16.00
Variable n5 = Control V5 * 32.00
Variable n6 = Control V6 * 64.00
Variable n7 = Control V7 * 128.0
Variable n8 = Control V8 * 256.0
Variable n9 = Control V9 * 512.0
Variable n10 = Control V10 * 1024
Variable n11 = Control V11 * 2048
Variable n12 = Control V12 * 4096
Variable n13 = Control V13 * 8192
Variable n14 = Control V14 * 16384
Variable n15 = Control V15 * 32768
Variable Dport = 0.00000
Variable Dport = Variable Dport + Variable n0
Variable Dport = Variable Dport + Variable n1
Variable Dport = Variable Dport + Variable n2
Variable Dport = Variable Dport + Variable n3
Variable Dport = Variable Dport + Variable n4
Variable Dport = Variable Dport + Variable n5
Variable Dport = Variable Dport + Variable n6
Variable Dport = Variable Dport + Variable n7
Variable Dport = Variable Dport + Variable n8
Variable Dport = Variable Dport + Variable n9
Variable Dport = Variable Dport + Variable n10
Variable Dport = Variable Dport + Variable n11
Variable Dport = Variable Dport + Variable n12
Variable Dport = Variable Dport + Variable n13
Variable Dport = Variable Dport + Variable n14
Variable Dport = Variable Dport + Variable n15
Variable previous = Variable Dport
VariableWash = Variable Dport + 1.000
If(Control bDR 1.000) then ...
   Variable selected = Control dAltvalv + Variable cnt2
   Jump to subroutine "ButoonSet"
   Variable cnt2 = 100000
   Variable Dport = 1.000
   While (Variable cnt3 < Variable selected) do ...
      Variable Dport = Variable Dport * 2.000
      Variable cnt3 Variable cnt3 + 1 .000
      While end
   If end
If(Control bDMD = 1.000) then...
   If (Variable cnt2 = 1.000) then...
      Variable selected = Control dAltvalv
      Jump to subroutine "ButsonSet"
      Variable cnt3 = 0.00000
      Variable Dport = 1.000
      While (Variable cnt3 < Control dAltvalv) do ...
         Variable Dport = Variable Dport * 2.000
         Variable cnt3 = Variable cnt3 + 1.000
         While end
      If end
   If end
Variable Dout = Variable Dport + 1.000
Fill wave Dout with - 1.0000, 24000 points
Dout = Dout = variable Vwash
Dseg2.3 = Dseg2.3 + 1.00000
Dseg2.3 = Dseg2.3 + variable Vwash
Dseg2.3 = Dseg2.3 = variable Dout
If(Variable cnt2 == 0.00000) then ...
   Fill wave 'DA0'with 0.0000O, 24000 points
   Variable vOut = Control cVCcom/ 20.00
   If(Control bMarkers == 1.000) then ...
      Vseg2.3 = Vseg2.3 + variable vOut
      If end
   If(Control bMarkers == 0.00000) then ...
      DA0 = DA0 + variable vOut
      If end
   If end
*******************************************************************************
Task:washvalv                                            Allow mouse activity
```

-continued

```
Task Begin
Variable Vwash = 1.000
Variable cnt1 = 0.00000
While (Variable cnt1 < Control dWashVlv) do...
   Variable Vwash = Variable Vwash * 2.000
   Variable cnt1 = Variable cnt1 + 1.000
   While end
*********************************************************************************
Task:timebase                                                      Allow mouse activity
Task Begin
Marker M4 & wave AD0 intersection (time to Marker4)
Variable_SampleP = 0.01000
Variable_TraceSi = Variable Marker4 Variable_SampleP
Variable_TraceSi = Variable_TraceSi * 10000
*********************************************************************************
Task:print                                                         Allow mouse activity
Task Begin
Choose Print_Under File
*********************************************************************************
Task:save                                                          Allow mouse activity
Task Begin
String_SaveWav = "" appended onto end of string""
String_SaveWav = date (e.g. "1/30/64")
String_SaveWav = ".AD1." appended onto end of string "String_SaveWav"
If (Variable tracenum < 10.00) then...
   String_SaveWav = "appended onto end of string " String_SaveWav"
   If end
If (Variable tracenum < 100.0) then .......
   String_SaveWav = "0" appended onto end of string "String_SaveWav"
   If end
String_SaveWav = "Variable tracenum" appended onto end of string "String_Save
Save wave AD1 to disk
*********************************************************************************
Task:setbuton                                                      Allow mouse activity
Task Begin
Control V0 = 0.00000
Control V1 = 0.00000
Control V2 = 0.00000
Control V3 = 0.00000
Control V4 = 0.00000
Control V5 = 0.00000
Control V6 = 0.00000
Control V7 = 0.00000
Control V8 = 0.00000
Control V9 = 0.00000
Control V10 = 0.00000
Control V11 = 0.00000
Control V12 = 0.00000
Control V13 = 0.00000
Control V14 = 0.00000
Control V15 = 0.00000
If(Variable selected == 0.00000) then ...
   Control V0 = 1.000
   If end
If(Variable selected == 1.000) then ...
   Control VI = 1.000
   If end
If (Variable selected == 2.000) then ...
   Control V2 = 1.000
   If end
If (Variable selected == 3.000) then ...
   Control V3 = 1.000
   If end
If (Variable selected == 4.000) then ...
   Control V4 = 1.000
   If end
If (Variable selected == 5.000) then ...
   Control V5 = 1.000
   If end
If (Variable selected == 6.000) then ...
   Control V6 = 1.000
   If end
If (Variable selected == 7.000) then ...
   Control V7 = 1.000
   If end
If (Variable selected == 8.000) then ...
   Control V8 = 1.000
   If end
If (Variable selected == 9.000) then ...
```

```
    Control V9 = 1.000
    If end
If (Variable selected == 10.00) then ...
    Control V10 = 1.000
    If end
If (Variable selected 11.00) then...
    Control V11 = 1.000
    If end
If (Variable selected == 12.00) then ...
    Control V12 = 1.000
    If end
If (Variable selected == 13.00) then ...
    Control V13 = 1.000
    If end
If (Variable selected == 14.00) then...
    Control V14 = 1.000
    If end
If (Variable selected == 15.00) then...
    Control V15 = 1.000
    If end
**************************************************************************************
Task:bDRtask                                                          Allow mouse activity
Task Begin
Variable selected = Control dAltvalv
Jump to subroutine "ButonSet"
Control bDMD = 0.00000
Control cVStep = 0.00000
Control sAuto = 0.00000
**************************************************************************************
Task:revpot                                                           Allow mouse activity
Task Begin
Control dEpiNum = 5.000
Control cVStep = 10.00
Control cVcom = 30.00
**************************************************************************************
Task:duration                                                         Allow mouse activity
Task Begin
Variable V39 = Control cWashtim * 60.00
Variable V40 = Variable Marker4 + Variable V39
Variable V41 = Variable V40 * Control dEpiNum
Variable timeV = Variable V41 / 60.00
Control iTime = Variable timeV
**************************************************************************************
Task:bDMDtask                                                         Allow mouse activity
Task Begin
Control bDR = 0.00000
Control cVStep = 0.00000
Control dEpiNum = 3.000
Control sAuto = 0.00000
**************************************************************************************
Task purge                                                            Allow mouse activity
Task Begin
Control bDR = 0.00000
Jump to subroutine "wash"
**************************************************************************************
Task:analyze                                                          Allow mouse activity
Task Begin
Flip = seg2.4 * -1.0e+9
Pulse analysis on Flip (min to wMin; max to wMax, tmax to wTmax)
String sTrace = "Variable tracenum" appended onto end of string "Trace #"
Append text onto the end of Journal1 with daa from string sTrace
String sTime = time (e.g. "10:31:02")
String sTime = "at" insert into "String sTime" after char 0 (base 1)
Append text onto the end of journal with data from string sTime
Insert"
"into journal Journal1
Insert "Valve" into journal Journal1
String sVwash = "/" appended onto end of string "Control dWashVlv"
Append text onto the end of Journal1 with data from string sVwash
Jumpt to subroutine "valvenum"
Append text onto the end of Journal1 with data from string sVdrug
Insert "Valve" into journal Journal1
String sVwash 2 = "" appended onto end of string "Control dWashVlv"
Append text onto the end of Journal1 with data from string sVwash2
Insert"
"into journal Journal1
Marker M2 & wave AD1 intersection (time to Marker 2)
Marker M3 & wave AD1 intersection (time to Marker 3)
Marker M4 & wave AD1 intersection (time to Marker 4)
```

-continued

```
String sM2 = "Variable Marker 2" rounded off to 1 digits after decimal
String sM2 = "M2 =" insert into "String sM2" after char 0 (base 1)
String sM3 = "Variable Marker 3" rounded off to 1 digits after decimal
String sM3 = ",M3 ="insert into "String sM3" after char 0 (base 1)
String sM4 = "Variable Marker 4"rounded off to 1 digits after decimal
String sM4 = ",M4 ="insert into "String sM4" after char 0 (base 1)
Append text onto the end of Journal1 with data from string sM2
Append text onto the end of Journal1 with data from string sM3
Append text onto the end of Journal1 with data from string sM4
Insert"
"into journal Journal1
String sVoffset = "Control cVcom" appended onto end of string "Vh offset = "
String sVoffset = "mV" appended onto end of string "String sVoffset
Append text onto the end of Journal1 with data from string sVoffset
Insert"
"into journal Journal1
Insert "Maximum =" into journal Journal1
String sMax = Variable wMax
String sMax = "String sMax" rounded off to 1 digits after decimal
String sMax = "nA at" appended onto end of string "String sMax"
String wTmax = "String wTmax" rounded off to 2 digits after decimal
String sMax = "String wTmax" appended onto end of string "String sMax"
String sMax = "s" appended onto end of string "String sMax"
Append text onto the end of Journal1 with data from string sMax
Insert"
"into journal Journal1
Variable wAmplitu = Variable wMax - Variable wMin
If(Control sGain == 1.000) then...
   Variable wAmplitu = Variable wAmplitu * 10.00
   If end
String sAmplitu = Variable wAmplitu
String sAmplitu = "String sAmplitu" rounded off to 0 digits after decimal
String sAmplitu = "nA" appended onto end of string "String sAmplitu"
Insert "Amplitude" = " into journal Journal1
Append text onto the end of Journal1 with data from string sAmplitu
Insert"
"into journal Journal1
Insert"
"into journal Journal1
*******************************************************************************
Task:overlay                                                    4Allow mouse activity
Task Begin
Variable V58 = Control dEpiNum
Variable V59 = Variable tracenum
Show Alert: "Overlay data from last trial?"
If (Variable error == 2.000) then ...
   Show Alert: "Start with what episode?"
   Variable V59 = String retValue
   Show Alert: "Overlay how many previous traces (2-7)?"
   Variable V58 = String netValue
   If end
Variable loadloop = 0.00000
If (Variable loadloop < Variable V58) then ...
   Jump to subroutine "MakeLoad"
   Load wave W1 from disk
   If end
If (Variable loadloop < Variable V58) then ...
   Jump to subroutine "MakeLoad"
   Load wave W2 from disk
   If end
If (Variable loadloop < Variable V58) then ...
   Jump to subroutine "MakeLoad"
   Load wave W3 from disk
   If end
If (Variable loadloop < Variable V58) then ...
   Jump to subroutine "MakeLoad"
   Load wave W4 from disk
   If end
If (Variable loadloop < Variable V58) then ...
   Jump to subroutine "MakeLoad"
   Load wave W5 from disk
   If end
If (Variable loadloop < Variable V58) then ...
   Jump to subroutine "MakeLoad"
   Load wave W6 from disk
   If end
If (Variable loadloop < Variable V58) then ...
   Jump to subroutine "MakeLoad"
   Load wave W7 from disk
```

-continued

```
If end
********************************************************************************
Task:loadwave                                                    Allow mouse activity
Task Begin
Choose Load Data_AD1 Under Wave
********************************************************************************
Task:_Startup                                                    4Allow mouse activity
Task Begin
Variable tracenum = 0.00000
Insert "Valve Assignments
0 Ringer
1 5 uM GABA
2 10 uM GABA
3 50 uM
********************************************************************************
Task:printjrn                                                    Allow mouse activity
Task Begin
Choose Print_Journal1 Under Journal
********************************************************************************
Task:clearjrn                                                    Allow mouse activity
Task Begin
Choose Clear Journal1 Under Journal
********************************************************************************
Task:sethresh                                                    Allow mouse activity
Task Begin
Open instruction number 3 in task analyze
********************************************************************************
Task:viewwave                                                    Allow mouse activity
Task Begin
Choose Edit then ... Fip Under Wave
********************************************************************************
Task:getVnum                                                     Allow mouse activity
Task Begin
String sVdrug = "" appended onto end of string""
If(Control V0 == 1.000) then...
   String sVdrug = "Valve 0" appended onto end of string "String sVdrug"
   If end
If(Control V1 == 1.000) then...
   String sVdrug = "Valve 1" appended onto end of string "String sVdrug"
   If end
If(Control V2 == 1.000) then...
   String sVdrug = "Valve 2" appended onto end of string "String sVdrug"
   If end
If(Control V3 == 1.000) then...
   String sVdrug = "Valve 3" appended onto end of string "String sVdrug"
   If end
If(Control V4 == 1.000) then...
   String sVdrug = "Valve 4" appended onto end of string "String sVdrug"
   If end
If(Control V5 == 1.000) then...
   String sVdrug = "Valve 5" appended onto end of string "String sVdrug"
   If end
If(Control V6 == 1.000) then...
   String sVdrug = "Valve 6" appended onto end of string "String sVdrug"
   If end
If(Control V7 == 1.000) then...
   String sVdrug = "Valve 7" appended onto end of string "String sVdrug"
   If end
If(Control V8 == 1.000) then...
   String sVdrug = "Valve 8" appended onto end of string "String sVdrug"
   If end
If(Control V9 == 1.000) then...
   String sVdrug = "Valve 9" appended onto end of string "String sVdrug"
   If end
If(Control V10 == 1.000) then...
   String sVdrug = "Valve 10" appended onto end of string "String sVdrug"
   If end
If(Control V11 == 1.000) then...
   String sVdrug = "Valve 11" appended onto end of string "String sVdrug"
   If end
If(Control V12 == 1.000) then...
   String sVdrug = "Valve 12" appended onto end of string "String sVdrug"
   If end
If(Control V13 == 1.000) then...
   String sVdrug = "Valve 13" appended onto end of string "String sVdrug"
   If end
If(Control V14 == 1.000) then...
   String sVdrug = "Valve 14" appended onto end of string "String sVdrug"
   If end
```

-continued

```
If(Control V15 == 1.000) then...
   String sVdrug = "Valve 15" appended onto end of string "String sVdrug"
   If end
*********************************************************************************
Task:smooth                                                        Allow mouse activity
Task Begin
AD1 = Smooth (AD1, 3.00000)
Variable vDel Seg = Variable Marker4 - 0.07000
AD1 = Delete (AD1, variable vDelSeg, variable Marker4)
*********************************************************************************
Task:setauto                                                       Allow mouse activity
Task Begin
If(Control dEpiNum > 1.000) then...
   Control sAuto = 0.00000
   If end
*********************************************************************************
Task:protocol                                                      Allow mouse activity
Task Begin
Control bDR = 0.00000
Control bDMD = 0.00000
Control dEpiNum = 1.000
Control cVcom = 0.00000
Control cVStep = 0.00000
Control dWashVlv = 0.00000
Control cWashtim = 0.5000
Control sGain = 0.00000
Control bVpulse = 0.00000
If(Control bP30s == 1.000) then...
   Move marker M4 to the 30.0000 position
   Move marker M3 to the 20.0000 position
   Move marker M2 to the 10.0000 position
   If end
If(Control bP60s == 1.000) then...
   Move marker M4 to the 60.0000 position
   Move marker M3 to the 40.0000 position
   Move marker M2 to the 20.0000 position
   If end
If(Control bIntPerf == 1.000) then...
   Move marker M4 to the 90.0000 position
   Move marker M3 to the 60.0000 position
   Move marker M2 to the 30.0000 position
   Control cVcom = 0.00000
   If end
*********************************************************************************
Task:header                                                        Allow mouse activity
Task Begin
If(Control bDR == 1.000) then...
   Insert "****Start Dose Response****" into journal Journal1
   Insert"
"into journal Journal1
   Insert"
"into journal Journal1
   If end
If(Control bDMD == 1.000) then...
   Insert "****Start D/M/D Protocol****" into journal Journal1
   Insert"
"into journal Journal1
   Insert"
"into journal Journal1
   If end
*********************************************************************************
Task:flush                                                         Allow mouse activity
Task Begin
Variable cnt4 = 1.000
While (Variable cnt4 <= control dEpi Num) do...
   Variable flushlp = Control dAltvalv +Control dEpiNum
   Variable flushlp = Variable fluship - Variable cnt4
   Variable Vflush = 1.000
   Variable cnt1 = 0.00000
   While (Variable cnt1 < Variable flushlp) do...
      Variable Vflush = Variable Vflush * 2.000
      Variable cnt1 = Variable cnt1 + 1.000
      While end
   Variable FlushOut = Variable Vflush + 1.000
   Variable FlushOut = Variable FlushOut * -1.00
   Cwrite (devType147, offset=192, slot=4; FlushOut to Value)
   Delay for 3.00000 seconds
   Cwrite (devType147, offset=192, slot=4; -1.00 to Value)
   Variable cnt4 = Variable cnt4 + 1.000
```

-continued

```
    While end
***************************************************************************
Task:oocytnew                                                    Allow mouse activity
Task Begin
Insert "New oocyte #
Rp = - at 1 mm
"into journal Journal1
***************************************************************************
Task:footer                                                      Allow mouse activity
Task Begin
If(Control bDR == 1.000) then...
    Insert "****End Dose Response****" into journal Journal1
    Insert "
"into journal Journal1
    Insert"
"into journal Journal1
    If end
If(Control bDMD == 1.000) then ...
    Insert "****End D/M/D Protocol****" into journal Journal1
    Insert "
"into journal Journal1
    Insert "
"into journal Journal1
    If end
***************************************************************************
Task:showhead                                                    Allow mouse activity
Task Begin
Choose Show jHeader Under Edit
***************************************************************************
Task:print_Jhd                                                   Allow mouse activity
Task Begin
Choose Print_jHeader Under Journal
***************************************************************************
Task:clearwav                                                    Allow mouse activity
Task Begin
Set wave W1 internals (0.00000 to #valid data pts)
Set wave W2 internals (0.00000 to #valid data pts)
Set wave W3 internals (0.00000 to #valid data pts)
Set wave W4 internals (0.00000 to #valid data pts)
Set wave W5 internals (0.00000 to #valid data pts)
Set wave W6 internals (0.00000 to #valid data pts)
Set wave W7 internals (0.00000 to #valid data pts)
***************************************************************************
Task:MakeLoad                                                    Allow mouse activity
Task Begin
Variable V57 = Variable V59 Variable loadloop
String_LoadWav = "" appended onto end of string ""
String_LoadWav = date (e.g. "1/30/64")
String_LoadWav = ".AD1." appended onto end of String "String_LoadWav"
If(Variable V57 < <10.00) then...
    String_LoadWav = "0" appended onto end of string "String_LoadWav"
    If end
IF(Variable V57 < 100.0) then...
    String_LoadWav = "0" appended onto end of string "String_LoadWav"
    If end
String_LoadWav = "Variable V57" 10 appended onto end of string "String_LoadWav"
Variable loadloop = Variable loadloop + 1.000
***************************************************************************
Task:markjrnl                                                    Allow mouse activity
Task Begin
Insert"****************
"into journal Journal1
***************************************************************************
Task:pRecord                                                     Allow mouse activity
Task Begin
Move marker M4 to the 118.000 position
Move marker M3 to the 110.000 position
Move marker M2 to the 10.0000 position
Control eWashtim = 0.00000
Control dEpiNum = 2.000
Control cVcom = 0.00000
***************************************************************************
Task:pCL.1                                                       Allow mouse activity
Task Begin
Move marker M4 to the 6.00000 position
Move marker M3 to the 4.00000 position
Move marker M2 to the 2.00000 position
Control cWashtim = 0.00000
Control dEpiNum = 10.00
```

-continued

```
Control cVcom = 50.0
Control cVStep = -10.0
Control sGain = 1.000
Control cWashtim = 0.00000
Control bVpulse = 1.000
Show Alert: "I(Cl) = V-dep. chloride current, activates on hyperpolarization
********************************************************************************
Task:pCL.2                                                        Allow mouse activity
Task Begin
Move marker M4 to the 6.00000 position
Move marker M3 to the 4.00000 position
Move marker M2 to the 2.00000 position
Control cWashtim = 0.00000
Control dEpiNum = 4.000
Control cVcom = 100.0
Control cVStep = 10.00
Control sGain = 0.00000
Control cWashtim = 0.00000
Control bVpulse = 1.000
Show Alert: "I(Cl(Ca)) = calcium-dep. chloride current, activates on depolar
********************************************************************************
Task:pIVcurve                                                     Allow mouse activity
Task Begin
Move marker M4 to the 6.00000 position
Move marker M3 to the 4.00000 position
Move marker M2 to the 2.00000 position
Control dEpiNum = 12.00
Control cVcom = 60.00
Control cVScep = -10.0
Control bGain = 0.00000
Control cWashtim = 0.00000
Control bMarkers = 1.000
Show Alert: "IV curve characterizes passive membrane (+10 mV to -100 mV). S
********************************************************************************
Task:pMemRes                                                      Allow mouse activity
Task Begin
Move marker M4 to the 6.00000 position
Move marker M3 to the 4.00000 position
Move marker M2 to the 2.00000 position
Control dEpiNum = 1.000
Control cVCcom = 10.00
Control cVCstep = 0.00000
Control bGain = 0.00000
Control cWashtim = 0.00000
Control bMarkers = 1.000
Show Alert: "Membrane resistance measurement. Applies +10 mV pulse, set Vh=
```

We claim:

1. A method for reproducibly detecting a response of a cell to an agent, the method comprising:
   a) providing an apparatus comprising:
      i) at least one recording chamber adapted to receive and support the cell;
      ii) a perfusion system adapted to perfuse said at least one recording chamber with a plurality of perfusion solutions each containing a different agent or concentration of an agent;
      iii) at least one invasive biosensor adapted to detect the response; and
      iv) a computer adapted to collect, analyze and display responses detected by said at least one biosensor;
      said apparatus having performance characteristics such that, starting at a physiological baseline, said apparatus being capable of determining a plateau response of a Xenopus oocyte to the application of 50 $\mu$M kainate in less than 10 seconds, and returning to baseline in less than an additional 10 seconds, the determination cycle being repeatable at least 60 times per hour for the life of the Xenopus oocyte;
   b) introducing a cell into the recording chamber;
   c) perfusing the cell with a plurality of perfusion solutions each containing a different agent or concentration of an agent;
   d) detecting the response of the cell to perfusions; and
   e) collecting, analyzing and displaying response data.

2. The method of claim 1 wherein the response of the cell to the agent is mediated by a cell surface receptor produced by recombinant DNA technology.

3. The method of claim 1 wherein said cell is a mammalian, insect, or amphibian cell.

4. The method of claim 1 wherein said cell is a Xenopus oocyte.

5. The method of claim 1 wherein said at least one recording chamber is a patch clamp pipet.

6. The method of claim 1 wherein said biosensor is an electrode.

7. The method of claim 6 wherein said electrode is a voltage measuring or a current injecting electrode.

8. The method of claim 6 wherein said electrode is a glass patch electrode.

9. The method of claim 6 wherein said electrode is an intracellular electrode.

10. The method of claim 1 further comprising an injecting means for delivering an injection solution into said cell.

11. The method of claim 1 wherein said perfusion system is an automated perfusion control system.

12. The method of claim 11 wherein said automated perfusion control system is a gravity fed flow through perfusion system.

13. The method of claim 11 wherein said automated perfusion control system comprises a plurality of reservoirs containing one or more different perfusion solutions; and a valve in fluid communication with said plurality of reservoirs for the delivery of said one or more different perfusion solution to said recording chamber.

14. The method of claim 13 wherein said plurality of reservoirs comprise between about 2 to about 100 reservoirs.

15. The method of claim 13 wherein said plurality of reservoirs comprise between about 6 to about 20 reservoirs.

16. The method of claim 12 wherein said automated perfusion control system further comprises a mixing means between said fluid valve and said recording chamber.

17. The method of claim 1 further comprising recording means for recording a said detected response from said biosensors.

18. The method of claim 17 wherein said recording means is selected from the group consisting of a digital recorder, a computer, volatile memory, involatile memory, chart recorder and combinations thereof.

19. The method of claim 1 further comprising means for controlling the temperature of said recording chamber.

20. The method of claim 1 further comprising means for controlling the oxygen, nitrogen, or carbon dioxide level of said recording chamber.

21. The method of claim 1 which is a tabletop unit with a weight of less than about 100 pounds.

22. The method of claim 1 wherein said computer is adapted for controlling said perfusion system.

23. The method of claim 1 further comprising means for receiving and automatically positioning a cell within said recording chamber and means for positioning said one or more biosensors to detect a response from said cell.

24. The method of claim 21, further comprising a single computer adapted to control said perfusion system and to collect, analyze and display responses detected by said at least one biosensor.

25. The method of claim 22, further comprising a computer usable medium having a computer readable program code embodied therein for causing said computer to operate said apparatus, said computer usable medium comprising:

a) computer readable program code means for controlling said perfusion system;

b) computer readable program code means for acquiring data from said at least one biosensor; and c) computer readable program code means for calculating in said computer, waveform analysis of said data.

* * * * *

UNITED STATES PATENT AND TRADEMARK OFFICE
CERTIFICATE OF CORRECTION

PATENT NO. : 6,268,168 B1
DATED : July 31, 2001
INVENTOR(S) : Farb et al.

It is certified that error appears in the above-identified patent and that said Letters Patent is hereby corrected as shown below:

<u>Claim 1</u>,
Line 9, delete "centration" and substitute therefor -- concentration --.

Signed and Sealed this

Ninth Day of April, 2002

*Attest:*

*Attesting Officer*

JAMES E. ROGAN
*Director of the United States Patent and Trademark Office*